US008170805B2

(12) United States Patent
Kishore et al.

(10) Patent No.: US 8,170,805 B2
(45) Date of Patent: May 1, 2012

(54) METHOD FOR SELECTING STATISTICALLY VALIDATED CANDIDATE GENES

(75) Inventors: Venkata Krishna Kishore, Bloomington, IL (US); Zhigang Guo, Champaign, IL (US); Min Li, Champaign, IL (US); Daolong Wang, Normal, IL (US); Libardo Andres Gutierrez Rojas, Northfield, MN (US); Joseph Dallas Clarke, V, Durham, NC (US); Joseph Byrum, West Des Monies, IA (US)

(73) Assignee: Syngenta Participations AG, Basel (CH)

( * ) Notice: Subject to any disclaimer, the term of this patent is extended or adjusted under 35 U.S.C. 154(b) by 472 days.

(21) Appl. No.: 12/367,045

(22) Filed: Feb. 6, 2009

(65) Prior Publication Data
US 2010/0204921 A1  Aug. 12, 2010

(51) Int. Cl.
*C12Q 1/68* (2006.01)
*G01N 33/48* (2006.01)
*G06G 7/58* (2006.01)

(52) U.S. Cl. .................... 702/19; 435/6; 702/20; 703/2; 703/11

(58) Field of Classification Search ........................ None
See application file for complete search history.

(56) References Cited

U.S. PATENT DOCUMENTS 5,569,588 A   10/1996  Ashby et al.
2007/0166707 A1   7/2007  Schadt et al.

OTHER PUBLICATIONS

Alberts, R., et al., "Sequence Polymorphisms Cause Many False cis eQTLs", *PLos ONE*, vol. 2, No. 7 (Jul. 2007), pp. 1-5.
Pearson, T.A., et al., "How to Interpret a Genome-Wide Assocaition Study", *JAMA*, vol. 299, No. 11 (Mar. 19, 2008), pp. 1335-1344.
Yu, J., et al., "Genetic Design and Statistical Power of Nested Association Mapping in Maize", *Genetics*, vol. 178 (Jan. 2008), pp. 539-551.
Alvarez-Castro et al., "A Unified Model for Functional and Statistical Epistasis and Its Application in Quantitative Trait Loci Analysis", Linnaeus Centre for Bioinformatics, Uppsala University, Uppsala, Sweden, *Genetics* 176: pp. 1151-1167 (Jun. 2007).
Anderson et al., "Domestic-Animal Genomics: Deciphering the Genetics of Complex Traits", www.nature.com/reviews/genetics ; Mar. 2004, vol. 5, pp. 202-212.
Bjornsson et al., "SNP-specific array-based allele-specific expression analysis", *Genome Research* 2008, 18: 771-779; downloaded from www.genome.cship.org on Nov. 1, 2010—Published by Cold Spring Harbor Laboratory Press.
Blanchard et al., "Sequence to array: Probing the genome's secrets", Analysis Research News; *Nature Biotechnology* vol. 14, p. 1649, Dec. 1996, Nature Publishing Group, http://www.nature.com/naturebiotechnology.
Blott et al., "Molecular Dissection of a Quantitative Trait Locus: A Phenylalanine-to-Tyrosine Substitution in the Transmembrane Domain of the Bovine Growth Hormone Receptor Is Associated With a Major Effect on Milk Yield and Composition", *Genetics* 163: 253-266 (Jan. 2003); Genetics Society of America.
Corrigendum—In the paper by Eric S. Lander and David Botstein (*Genetics* 121: 185-199; Jan. 1989) entitled "Mapping Mendelian Factors Underlying Quantitative Traits Using RFLP Linkage Maps," the authors wish to correct two typographic errors in the statement of Proposition 2 on p. 192. (705).
Darvasi et al., "The beauty of admixture", *Nature Genetics*, vol. 37, No. 2, Feb. 2005, pp. 118-119.
Doerge, "Mapping and Analysis of Quantitative Trait Loci in Experimental Populations", Nature Reviews, *Genetics*, vol. 3, Jan. 2002, pp. 43-52, 2001 Macmillian Magazines Ltd.
Falush et al., "Inference of Population Structure Using Multilocus Genotype Data: Linked Loci and Correlated Allele Frequencies", *Genetics* 164: 1567-1587 (Aug. 2003); Genetics Society of America.
Flint et al., "Strategies for Mapping and Cloning Quantitative Trait Genes in Rodents", Nature Reviews, *Genetics*, vol. 6, Apr. 2005, pp. 271-286, Nature Publishing Group.
Haley et al., "A simple regression method for mapping quantitative trait loci in line crosses using flanking markers", *Heredity* 69 (1991) 315-324; The Genetical Society of Great Britain.
Hirschhorn et al., "Genome-Wide Association Studies for Common Diseases and Complex Traits", Nature Reviews, *Genetics*, vol. 6, Feb. 2005, pp. 95-108, Nature Publishing Group.
Jansen et al., "Mapping Quantitative Trait Loci in Plant Breeding Populations: Use of Parental Haplotype Sharing", *Crop Science* 43:829-834 (2003).
Jansen, "A general mixture model for mapping quantitative trait loci by using molecular markers", Centre for Plant Breeding and Reproduction Research, Wageningen, The Netherlands, *Theoretical and Applied Genetics* (1992) 85: 252-260, Springer-Verlag.
Jansen, "A General Monte Carlo Method for Mapping Multiple Quantitative Trait Loci", Centre for Plant Breeding and Reproduction Research, Wageningen, The Netherlands; *Genetics* 142: 305-311 (Jan. 1996), Genetics Society of America.

(Continued)

*Primary Examiner* — Shubo Zhou
(74) *Attorney, Agent, or Firm* — Myers Bigel Sibley & Sajovec, P.A.

(57) ABSTRACT

Provided herein are methods for evaluating associations between candidate genes and a trait of interest in a population. The methods include a combination of genome-wide association analysis and one or more of nested association mapping (NAM), expression QTL analysis (eQTL), and allele epistastic analysis (AEA). Markers are selected or prioritized if they are shown to be positively-correlated with a trait of interest using GWA and a combination of one or both of NAM and eQTL. Also provided are models for evaluating the association between a candidate marker and a trait in a nested population of organisms. These methods include single marker regression and multiple marker regression models. Markers identified using the methods of the invention can be used in marker assisted breeding and selection, as genetic markers for constructing linkage maps, for gene discovery, for identifying genes contributing to a trait of interest, and for generating transgenic organisms having a desired trait.

8 Claims, 5 Drawing Sheets

OTHER PUBLICATIONS

Jansen, Complex plant traits: time for polygenic analysis, Trends in Plant Science—Reviews, Mar. 1996, vol. 1, No. 3, pp. 89-94, Elsevier Science Ltd.

Jansen, "Controlling the Type I and Type II Errors in Mapping Quantitative Trait Loci", Centre for Plant Breeding and Reproduction Research, Wageningen, The Netherlands, *Genetics* 138: 871-881 (Nov. 1994); Genetics Society of America.

Jansen, "Genotype-by-environment interaction in genetic mapping of multiple quantitative trait loci", *Theoretical and Applied Genetics* (1995) 91:33-37, Springer-Verlag.

Jansen, "Interval Mapping of Multiple Quantitative Trait Loci", Centre for Plant Breeding and Reproduction Research, Wageningen, The Netherlands; *Genetics* 135: 205-211 (Sep. 1993), Genetics Society of America.

Kruglyak et al., "A Nonparametric Approach for Mapping Quantitative Trait Loci", Cambridge, Massachusetts; *Genetics* 139:1421-1428 (Mar. 1995), Genetics Society of America.

Lander et al., "Genetic Dissection of Complex Traits", FOCUS—The Journal of Lifelong Learning in Psychiatry, Summer 2006, vol. IV, No. 3, pp. 442-458.

Lander et al., "Mapping Mendelian Factors Underlying Quantitative Traits Using RFLP Linkage Maps", *Genetics* 121: 185-199 (Jan. 1989) Genetics Society of America.

Li et al., "Combining Data From Multiple Inbred Line Crosses Improves the Power and Resolution of Quantitative Trait Loci Mapping", Bar Harbor, Maine, *Genetics* 169: 1699-1709 (Mar. 2005), Genetics Society of America.

Lo et al., "Allelic Variation in Gene Expression Is Common in the Human Genome", *Genome Research* 2003, 13: 1855-1862; downloaded from www.genome.cship.org on Nov. 1, 2010—Published by Cold Spring Harbor Laboratory Press.

Lockhart et al., "Expression monitoring by hybridization to high-density oligonucleotide arrays", *Nature Biotechnology*, vol. 14, Dec. 1996, Nature Publishing Group, http://nature.com/naturebiotechnoloqy, p. 1675-1680.

Meuwissen et al., "Fine Mapping of a Quantitative Trait Locus for Twinning Rate Using Combined Linkage and Linkage Disequilibrium Mapping," *Genetics* 161: 373-379 (May 2002), Genetics Society of America.

Mott et al., "Simultaneous Detection and Fine Mapping of Quantitative Trait Loci in Mice Using Heterogeneous Stocks", *Genetics* 160: 1609-1618 (Apr. 2002), Genetics Society of America.

Notification of Transmittal of the International Search Report and the Written Opinion of the International Searching Authority, or the Declaration; International Search Report; Written Opinion of the International Searching Authority; Date of mailing: Jul. 15, 2010, 19 pages.

Pant et al., "Analysis of allelic differential expression in human white blood cells", *Genome Research* 2006 16: 331-339; downloaded from www.genome.cship.org on Nov. 1, 2010—Published by Cold Spring Harbor Laboratory Press.

Parisseaux et al., "In silico mapping of quantitative trait loci in maize", Theor Appl Genet (2004) 109: 508-514, Springer-Verlag.

Rebai et al., "More about quantitative trait loci mapping with diallel designs", *Genet. Res. Camb*. (2000), 75, pp. 243-247, Printed in the United Kingdom, Cambridge University Press.

Reiter et al., "Global and local genome mapping in *Arabidopsis thaliana* by using recombinant inbred lines and random amplified polymorphic DNAs", *Proc. Natl. Acad. Sci. USA*, vol. 89, pp. 1477-1481, Feb. 1992, Genetics.

Verhoeven et al., "Using mating designs to uncover QTL and the genetic architecture of complex traits", *Heredity* (2006) 96, 139-149, Nature Publishing Group, www.nature.com/hdy.

Walsh, Lecture 8—"Qtl Mapping 1: Overview and Using Inbred Lines", Jun. 2008; Summer Institute on Statistical Genetics, Seattle; pp. 1-13.

Walsh, Lecture 9—QTL and Association Mapping in Outbred Populations, Jun. 2008, Summer Institute on Statistical Genetics, Seattle; pp. 1-18.

Wu et al., "Joint Linkage and Linkage Disequilibrium Mapping in Natural Populations", *Genetics* 157: 899-909 (Feb. 2001), Genetics Society of America.

Wu et al., "Joint Linkage and Linkage Disequilibrium Mapping of Quantitative Trait Loci in Natural Populations", *Genetics* 160: 779-792 (Feb. 2002), Genetics Society of America.

Xu, "Mapping Quantitative Trait Loci Using Multiple Families of Line Crosses", *Genetics* 148: 517-524 (Jan. 1998), Genetics Society of America.

Yi et al., "Linkage analysis of quantitative trait loci in multiple line crosses", Genetica 114: 217-230; 2002 Kluwer Academic Publishers.

Yu et al., "A unified mixed-model method for association mapping that accounts for multiple levels of relatedness", *Nature Genetics*; vol. 38, No. 2, Feb. 2006, p. 203-208.

Zeng, "Precision Mapping of Quantitative Trait Loci", Genetics 136: 1457-1468 (Apr. 1994), Genetics Society of America.

Zeng, "Theoretical basis for separation of multiple linked gene effects in mapping quantitative trait loci", *Proc. Natl. Acad. Sci. USA*; vol. 90, pp. 10972-10976, Dec. 1993, Genetics.

Bennewits, et al., "Multiple Quantitative Trait Loci Mapping With Cofactors and Application of Alternative Variants of the False Discovery Rate in an Enlarged Granddaughter Design", *Genetics*, 2004, pp. 1019-1027, vol. 168.

Gieger, et al., "Genetics Meets Metabolomics: A Genome-Wise Assocation Study of Metabolite Profiles in Human Serum", *PLoS Genetics*, 2008, pp. 1-12, vol. 4, No. 11.

Yu, et al., "A Unified Mixed-Model Method for Association Mapping That Accounts for Multiple Levels of Relatedness," *Nature Genetics*, 2006, pp. 203-208, vol. 38, No. 2.

Buckler et al. "The Genetic Architecture of Maize Flowering Time" *Science* 325:714-718 (2009).

Darvasi et al. "Detecting Marker-QTL Linkage and Estimating QTL Gene Effect and Map Location Using a Saturated Genetic Map" *Genetics* 134:943-951 (1993).

Zeng. "Precision Mapping of Quantitative Trait Loci" *Genetics* 136:1457-1468 (1994).

International Preliminary Report on Patentability for International Application No. PCT/US2010/023312, mailed Aug. 18, 2011 (11 pages).

METHOD FOR SELECTING STATISTICALLY VALIDATED CANDIDATE GENES

FIELD OF THE INVENTION

This invention relates molecular genetics, particularly to methods for evaluating an association between a genetic marker and a phenotype in a population.

BACKGROUND OF THE INVENTION

Multiple experimental paradigms have been developed to identify and analyze quantitative trait loci (QTL) (see, e.g., Jansen (1996) Trends Plant Sci 1:89). A quantitative trait locus (QTL) is a region of the genome that codes for one or more proteins and that explains a significant proportion of the variability of a given phenotype that may be controlled by multiple genes. The majority of published reports on QTL mapping in crop species have been based on the use of the bi-parental cross. Typically, these paradigms involve crossing one or more parental pairs, which can be, for example, a single pair derived from two inbred strains, or multiple related or unrelated parents of different inbred strains or lines, each of which exhibits different characteristics relative to the phenotypic trait of interest. Typically, this experimental protocol involves deriving 100 to 300 segregating progeny from a single cross of two divergent inbred lines (e.g., selected to maximize phenotypic and molecular marker differences between the lines). The parents and segregating progeny are genotyped for multiple marker loci and evaluated for one to several quantitative traits (e.g., disease resistance). QTL are then identified as significant statistical associations between genotypic values and phenotypic variability among the segregating progeny.

Numerous statistical methods for determining whether markers are genetically linked to a QTL (or to another marker) are known to those of skill in the art and include, e.g., standard linear models, such as ANOVA or regression mapping (Haley and Knott (1992) Heredity 69:315), maximum likelihood methods such as expectation-maximization algorithms, (e.g., Lander and Botstein (1989) Genetics 121:185-199; Jansen (1992) Theor. Appl. Genet., 85:252-260; Jansen (1993) Biometrics 49:227-231; Jansen (1994) In J. W. van Ooijen and J. Jansen (eds.), Biometrics in Plant breeding: applications of molecular markers, pp. 116-124, CPRO-DLO Netherlands; Jansen (1996) Genetics 142:305-311; and Jansen and Stam (1994) Genetics 136:1447-1455). Exemplary statistical methods include single point marker analysis, interval mapping (Lander and Botstein (1989) Genetics 121: 185), composite interval mapping, penalized regression analysis, complex pedigree analysis, MCMC analysis, MQM analysis (Jansen (1994) Genetics 138:871), HAPLO-IM+ analysis, HAPLO-MQM analysis, and HAPLO-MQM+ analysis, Bayesian MCMC, ridge regression, identity-by-descent analysis, and Haseman-Elston regression.

Complex trait dissection in many species has largely relied on two main approaches, linkage analysis and association mapping (Andersson and Georges 2004, Nat. Rev. Genet. 5: 202-212; Flint et al. 2005, Nat. Rev. Genet. 6: 271-286; Hirschhorn and Daly 2005, Nat. Rev. Genet. 6: 95-108). While methods for linkage analysis using designed mapping populations have long been employed (Doerge 2002, Nat. Rev. Genet. 3: 43-52), methods for association mapping with population-based samples were more recently developed to overcome the hidden population structure or cryptic relatedness within collected samples (Falush et al. 2003, Genetics 164: 1567-1587; Yu et al. 2006, Nat. Genet. 38: 203-208). Statistical methods for joint linkage and linkage-disequilibrium mapping strategy have been studied for natural populations (Wu and Zeng 2001, Genetics 157: 899-909; Wu et al. 2002, Genetics 160: 779-792) and crossing an inbred to a heterogeneous stock has also been examined (Mott and Flint 2002, Genetics 160: 1609-1618). For a general complex pedigree, fine mapping via combining linkage and linkage-disequilibrium information at previously mapped QTL regions has identified candidate gene polymorphisms (Meuwissen et al. 2002, Genetics 161: 373-379; Blott et al. 2003, Genetics 163: 253-266). Previous studies of genetic designs with multiple line crosses have shown an improved power and mapping resolution over a single population (Rebai and Goffinet 1993, Genet. Res. 75: 243-247; Xu 1998, Genetics 148: 517-524; Rebai and Goffinet 2000, Genet. Res. 75: 243-247; Yi and Xu 2002, Genetica 114: 217-230; Jansen et al. 2003, Crop Sci. 43: 829-834; Li et al. 2005, Genetics 169: 1699-1709; Verhoeven et al. 2006, Heredity 96: 139-149). These studies, however, exploited mainly the linkage information of multiple line crosses.

In the case of humans, the use of genetics to identify genes and pathways associated with traits follows a very standard paradigm. First, a genome-wide linkage study is performed using hundreds of genetic markers in family-based data to identify broad regions linked to the trait. The result of this standard sort of linkage analysis is the identification of regions controlling for the trait, thereby restricting attention from the 30,000 plus genes to perhaps as few as 500 to 1000 genes in a particular region of the genome that is linked to the trait. However, the regions identified using linkage analysis are still far too broad to identify candidate genes associated with the trait. Therefore, such linkage studies are typically followed up by fine mapping the regions of linkage using higher density markers in the linkage region, increasing the number of families in the analysis, and identifying alternative populations for study. These efforts further restrict attention to narrower regions of the genome, on the order of 100 genes in a particular region linked to the trait. Even with the more narrowly defined linkage region, the number of genes to validate is still unreasonably large. Therefore, research at this stage focuses on identifying candidate genes based on putative function of known or predicted genes in the region and the potential relevance of that function to the trait. This approach is problematic because it is limited to what is currently known about genes. Often, such knowledge is limited and subject to interpretation. As a result, researchers are often led astray and do not identify the genes affecting the trait.

SUMMARY OF THE INVENTION

The invention includes evaluating or validating associations between candidate genes and a trait of interest in a plant population. The methods of the invention comprise a unique combination of genome-wide association (GWA) analysis and one or both of nested association mapping (NAM) and expression QTL analysis (eQTL) for selection and prioritization of candidate markers for further implementation or use. Markers are selected if they are shown to be positively-correlated with a trait of interest using GWA and a combination of one or both of NAM and eQTL.

Further provided are novel regression models for nested association mapping. These methods comprise a single marker regression model (SMR) and a multiple marker regression model (MRM). In some embodiments, non informative genotypes are removed prior to evaluating an association between a trait value and a marker genotype using the SMR model. In other embodiments, stepwise regression is used to select cofactor markers for inclusion in the MMR model. In various aspects of the invention, markers are considered for further validation if an association is detected using either SMR or MMR, or both.

Markers identified, selected, or validated using the methods of the invention can be used in marker assisted breeding and selection, as genetic markers for constructing genetic linkage maps, to isolate genomic DNA sequence surrounding a gene-coding or non-coding DNA sequence, to identify genes contributing to a trait of interest, and for generating transgenic organisms having a desired trait.

DETAILED DESCRIPTION OF THE INVENTION

Overview

Figure 1:
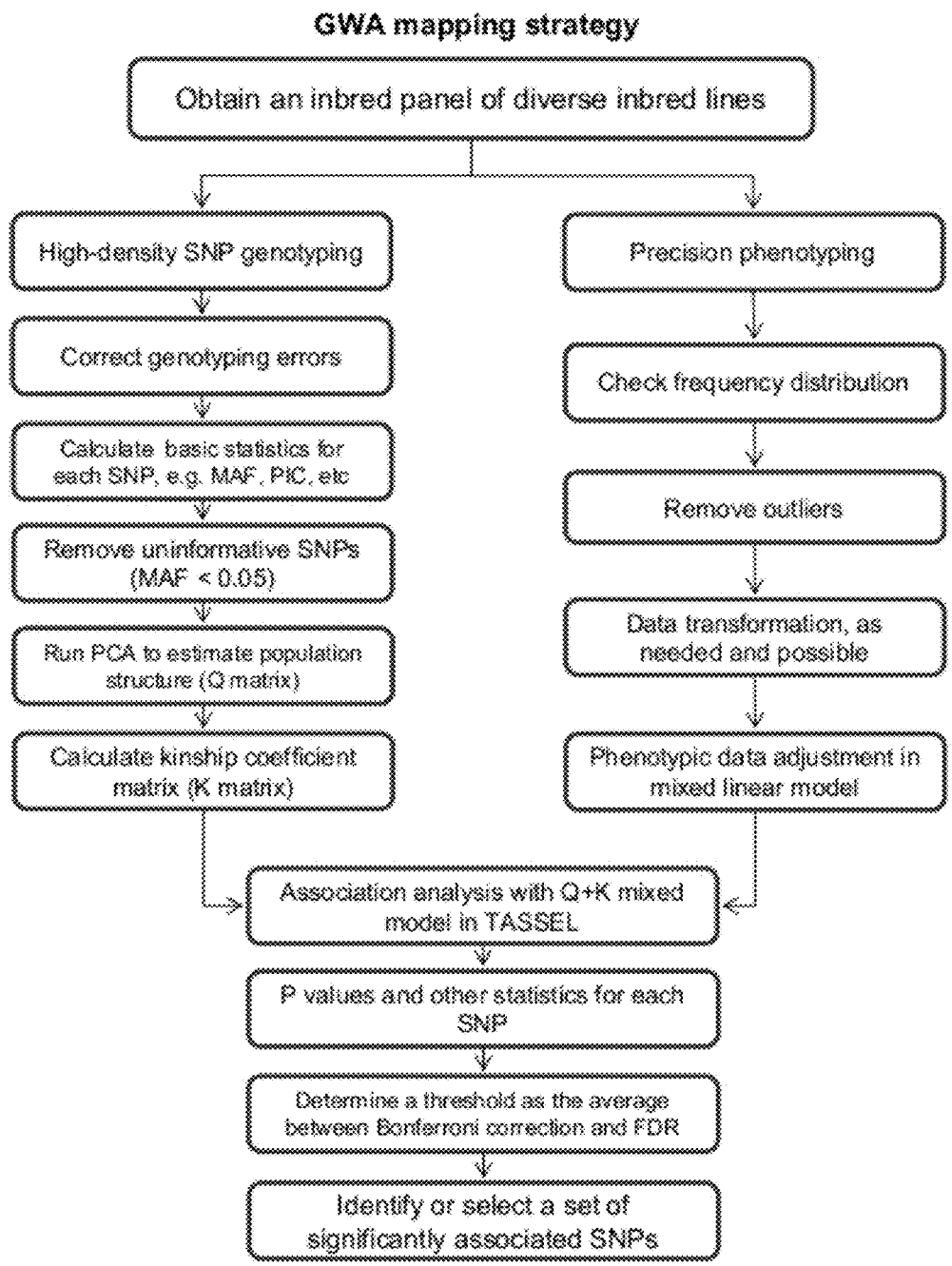
FIG. 1 is an exemplary flow chart depicting the steps involved in GWA.
Figure 2:
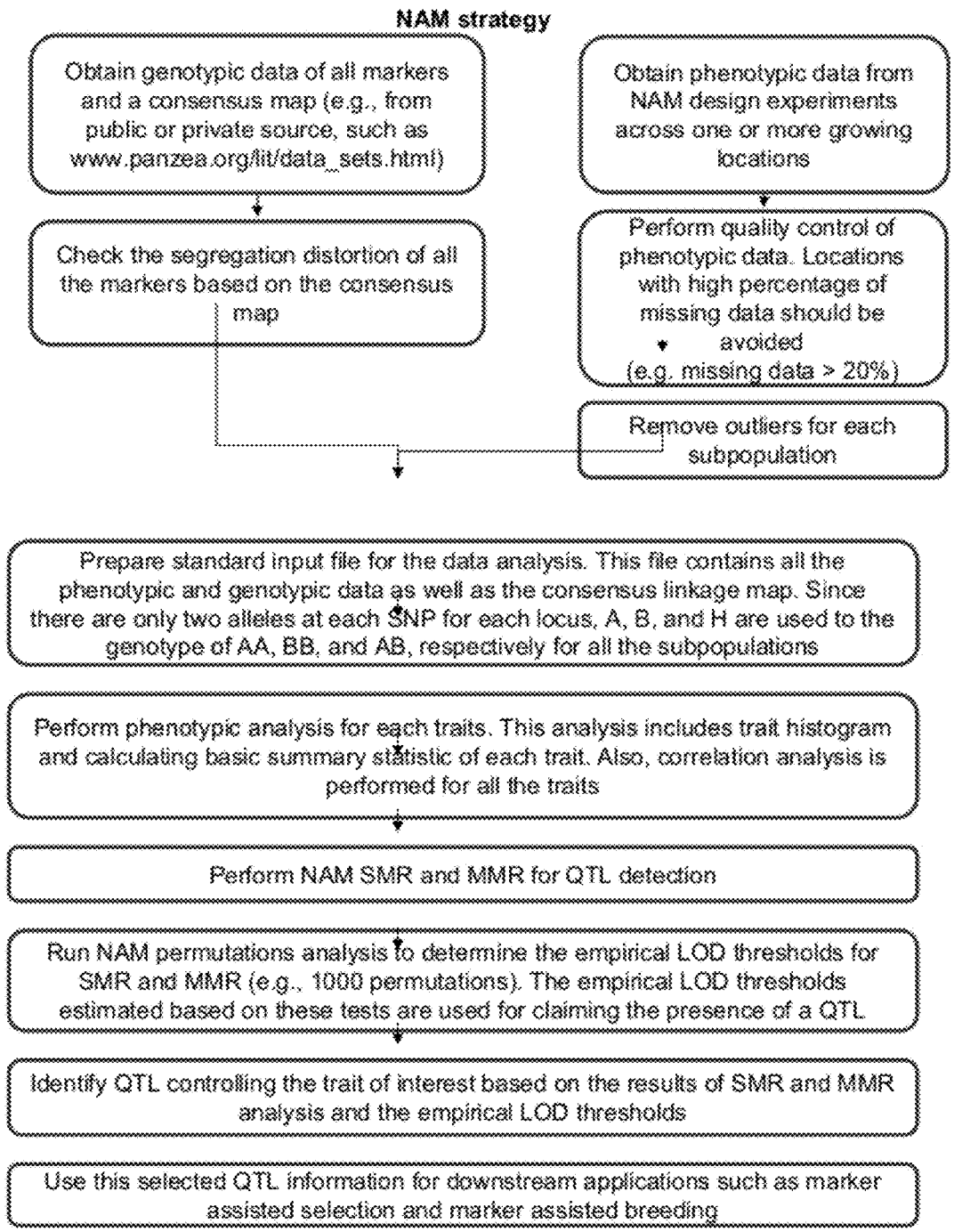
FIG. 2 is an exemplary flow chart depicting the steps involved in NAM.
Figure 3:
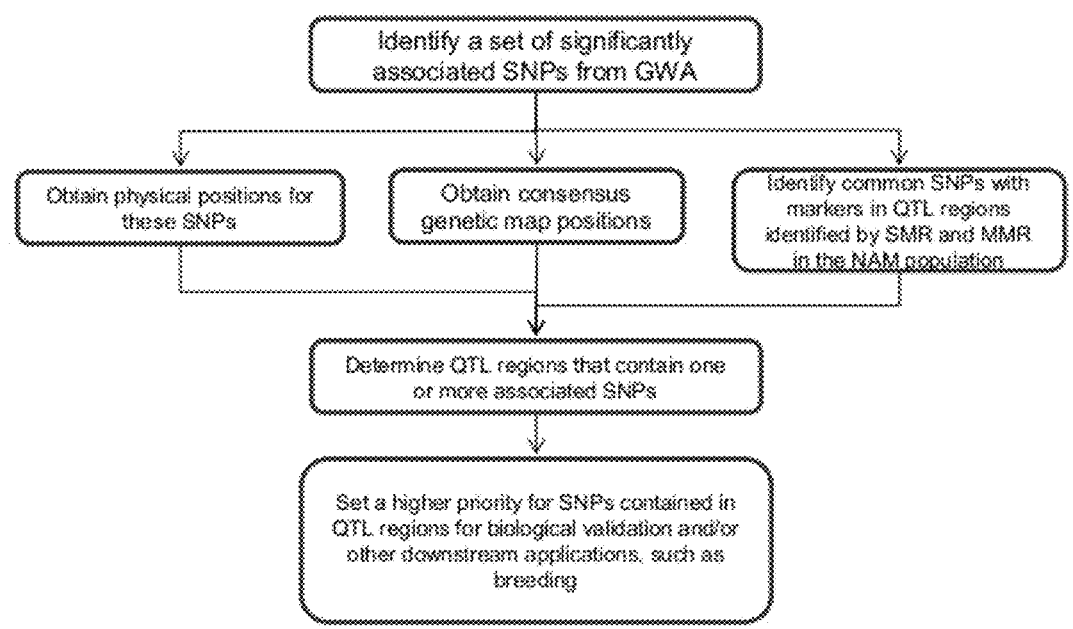
FIG. 3 is an exemplary flow chart depicting the steps involved in combining GWA and NAM for selecting and prioritizing a candidate marker for downstream use.

Estimation of the positions and effects of quantitative trait loci (QTL) is of central importance for marker assisted selection. Up to now, this has been accomplished by classical QTL mapping approaches (Lander and Botstein (1989) Genetics 121:185-199). The necessary experiments require establishment as well as pheno- and genotyping of large mapping populations and, thus, are very cost and time intensive (Parisseaux and Bernardo (2004) Theor Appl Genet 109:508-514).

Described herein is a method of discovering or validating an association between one or more candidate genes and a phenotypic trait of interest. In various embodiments of the present invention, markers are selected, validated, or prioritized for downstream use by comparing positively-correlated markers identified using genome-wide association analysis (GWA) with positively-correlated markers using other association models such as nested association mapping (NAM) and/or expression QTL (eQTL) analysis. Positively-correlated markers identified using GWA and one or both of NAM and eQTL analysis are placed on a physical genetic map of the species under study. Markers are prioritized for further use if they are identified in both GWA methods and one or both of NAM and eQTL (i.e., "overlapping" markers). Thus, the methods disclosed herein facilitate prioritization of candidate markers for selection and implementation in downstream processes to increase the chances of success in developing diagnostic markers for marker assisted breeding and product development.

Further provided herein are novel methods for nested association mapping (NAM). NAM is a method for evaluating the association between a candidate marker and a trait of interest in a nested population of organisms. The methods comprise novel single and multiple regression models for evaluating an association between a candidate gene and a trait of interest in a nested population.

For the purposes of the present invention, a "candidate gene" is intended a gene or genetic element that is being tested for an association between the gene and a trait of interest. The candidate gene may be an ortholog of a gene known or suspected to be associated with the trait of interest in a different species. As used herein, the term "associated with" in connection with a relationship between a genetic marker (SNP, haplotype, insertion/deletion, tandem repeat, etc.) and a phenotype refers to a statistically significant dependence of marker frequency with respect to a quantitative scale or qualitative gradation of the phenotype. A marker "positively" correlates with a trait when it is linked to it and when presence of the marker is an indicator that the desired trait or trait form will occur in an organism comprising the marker. A marker negatively correlates with a trait when it is linked to it and when presence of the marker is an indicator that a desired trait or trait form will not occur in an organism comprising the marker. For the purposes of the present invention, the term "marker" refers to any genetic element that is being tested for an association with a trait of interest, and does not necessarily mean that the marker is positively or negatively correlated with the trait of interest.

Thus, a marker is associated with a trait of interest when the marker genotypes and trait phenotypes are found together in the progeny of an organism more often than if the marker genotypes and trait phenotypes segregated separately. The phrase "phenotypic trait" refers to the appearance or other characteristic of an organism, e.g., a plant or animal, resulting from the interaction of its genome with the environment. The term "phenotype" refers to any visible, detectable or otherwise measurable property of an organism. The term "genotype" refers to the genetic constitution of an organism. This may be considered in total, or with respect to the alleles of a single gene, i.e. at a given genetic locus.

In some embodiments, the markers are candidate genes or genetic elements directly attributable to the phenotypic trait. For example, a genetic element directly attributable to starch accumulation in a plant may be a gene directly involved in plant starch metabolism. Alternatively, the marker may be found within a genetic locus associated with the phenotypic trait of interest. A "locus" is a chromosomal region where a polymorphic nucleic acid, trait determinant, gene or marker is located. Thus, for example, a "gene locus" is a specific chromosome location in the genome of a species where a specific gene can be found. In various embodiments, the markers identified or validated using the methods disclosed herein may be associated with a quantitative trait locus (QTL). The term "quantitative trait locus" or "QTL" refers to a polymorphic genetic locus with at least two alleles that differentially affect the expression of a phenotypic trait in at least one genetic background.

In some aspects, the candidate genes identified or validated using the methods described herein are linked or closely linked to QTL markers. The phrase "closely linked," in the present application, means that recombination between two linked loci occurs with a frequency of equal to or less than about 10% (i.e., are separated on a genetic map by not more than 10 cM). In other words, the closely linked loci co-segregate at least 90% of the time. Marker loci are especially useful in the present invention when they demonstrate a significant probability of co-segregation (linkage) with a desired trait. In some aspects, these markers can be termed linked QTL markers.

The methods disclosed herein incorporate a variety of statistical tests and models which may not be explicitly described herein. A thorough description of standard statistical tests can be found in basic textbooks on statistics such as, for example, Dixon, W. J. et al., Introduction to Statistical Analysis, New York, McGraw-Hill (1969) or Steel R. G. D. et al., Principles and Procedures of Statistics: with Special Reference to the Biological Sciences, New York, McGraw-Hill (1960). There are also a number of software programs for statistical analysis that are known to one skilled in the art.

Population of Interest

The methods of the present invention comprise identifying or validating a candidate marker by performing genome-wide association analysis (GWA) on a population of organisms (e.g., plant or animal), and comparing any positively-correlated markers in the GWA analysis with markers determined to have a positive correlation with the trait of interest in the same species of the organism using one or both of nested association mapping (NAM) and expression QTL (eQTL) analysis. Candidate markers are prioritized for further use or implementation (e.g., marker-assisted breeding, transgenic plant development, and the like) when the marker is shown to have a positive correlation in the GWA analysis and at least one other linkage analysis method, for example, at least one of eQTL analysis, NAM, or AEA. It is not necessary that the same mapping population be used for each analysis, so long as the population for all studies consists of plants of the same species.

A majority of published reports on QTL mapping in crop species has been based on the use of the bi-parental cross (Lynch and Walsh (1997) Genetics and Analysis of Quantitative Traits Sinauer Associates, Sunderland). Typically, this experimental protocol involves deriving 100 to 300 segregating progeny from a single cross of two divergent inbred lines (e.g., selected to maximize phenotypic and molecular marker differences between the lines). The segregating progeny are genotyped for multiple marker loci and evaluated for one to several quantitative traits in several environments. QTL are then identified as significant statistical associations between genotypic values and phenotypic variability among the segregating progeny.

The methods provided herein are useful for discovering or validating marker: trait associations in any population. The term "population" or "population of organisms" indicates a group of organisms of the same species, for example, from which samples are taken for evaluation, and/or from which individual members are selected for breeding purposes. The population members from which the markers are assessed need not be identical to the population members ultimately selected for breeding to obtain progeny, e.g., progeny used for subsequent cycles of analysis. While the methods disclosed herein are exemplified and described primarily using plant populations, the methods are equally applicable to animal populations, for example, humans and non-human animals, such as laboratory animals, domesticated livestock, companion animals, etc.

In embodiments of the invention, the organism population, such as a plant population, comprises or consists of a population resulting from crosses between one or more founder lines and a single common parent line. In various embodiments, the single common parent line is a tester line. The phrase "tester line" refers to a line that is unrelated to and genetically different from a set of lines to which it is crossed. Using a tester parent in a sexual cross allows one of skill to determine the association of phenotypic trait with expression of quantitative trait loci in a hybrid combination. The phrase "hybrid combination" refers to the process of crossing a single tester parent to multiple lines. The purpose of producing such crosses is to evaluate the ability of the lines to produce desirable phenotypes in hybrid progeny derived from the line by the tester cross.

The progeny of the cross between the founder lines and the tester line undergo multiple rounds of "selfing" to generate a population segregating for all genes in a Mendelian fashion. This mapping population is referred to herein as the "nested population" and is useful for the particular embodiment of the invention that implements nested associated mapping (NAM) methods, for example, the novel NAM methods described herein. These recombinant inbred lines (RIL) (genetically related lines; usually >$F_5$, developed from continuously selfing $F_2$ lines towards homozygosity) can be used as the mapping population. Information obtained from dominant markers can be maximized by using RIL because all loci are homozygous or nearly so. Under conditions of tight linkage (i.e., about <10% recombination), dominant and co-dominant markers evaluated in RIL populations provide more information per individual than either marker type in backcross populations (Reiter et al., Proc. Natl. Acad. Sci. (U.S.A.) 89:1477-1481 (1992)).

The term "crossed" or "cross" in the context of this invention means the fusion of gametes via pollination to produce progeny (e.g., cells, seeds or plants). The term encompasses both sexual crosses (e.g., the pollination of one plant by another, or the fertilization of one gamete by another) and selfing (e.g., self-pollination, e.g., when the pollen and ovule are from the same plant). The phrase "hybrid" refers to organisms which result from a cross between genetically divergent individuals. The phrase "inbred" refers to organisms derived from a cross between genetically related individuals. The term "lines" in the context of this invention refers to a family of related plants derived by self-pollinating an inbred plant. The term "progeny" refers to the descendants of a particular organism (e.g., self crossed plants) or pair of organisms (e.g., through sexual crossing). The descendants can be, for example, of the $F_1$, the $F_2$ or any subsequent generation.

The methods disclosed herein further encompass a hybrid cross between a tester line and an elite line. An "elite line" or "elite strain" is an agronomically superior line that has resulted from many cycles of breeding and selection for superior agronomic performance. In contrast, an "exotic strain" or an "exotic germplasm" is a strain or germplasm derived from an organism not belonging to an available elite line or strain of germplasm. Numerous elite lines are available and known to those of skill in the art of breeding. An "elite population" is an assortment of elite individuals or lines that can be used to represent the state of the art in terms of agronomically superior genotypes of a given species. Similarly, an "elite germplasm" or elite strain of germplasm is an agronomically superior germplasm, typically derived from and/or capable of giving rise to an organism with superior agronomic performance. The term "germplasm" refers to genetic material of or from an individual (e.g., a plant or animal), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture.

In some instances, a population may include parental organisms as well as one or more progeny derived from the parental organisms. In some instances, a population is derived from a single biparental cross, e.g., a population of progeny of a cross between two parents. Alternatively, a population includes members derived from two or more crosses involving the same or different parents. The population may consist of recombinant inbred lines, backcross lines, testcross lines, and the like.

In various embodiments, the population is a plant population consisting of early stage breeding materials. By "early stage" breeding material is intended that the plants are in the F2 to the F3 generation. The use of early stage breeding materials finds advantage in that the number of available breeding materials is large; the phenotypic data is available for the breeding lines; and the mapping results may directly help with selection. In the early stages of breeding, multiple lines are tested in multiple locations.

Because early breeding stages involve the evaluation of large numbers of progeny derived from multiple crosses, they provide the necessary phenotypic data for identifying and validating markers for a wide range of agronomic traits. By integrating marker analyses into existing breeding programs, the power, precision and accuracy associated with large numbers of progeny can be attained. Furthermore, inferences about marker associations can be drawn across the breeding program rather than being limited to the sample of progeny from a single cross.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al., Proc. Natl. Acad. Sci. (U.S.A.) 89:1477-1481 (1992)). Information obtained from backcross populations using either co dominant or dominant markers are less than that obtained from $F_2$ populations because one, rather than two, recombinant gametes are sampled per plant. Backcross populations, however, are more informative (at low marker saturation) when compared to RILs as the distance between linked loci increases in RIL populations (i.e. about 0.15% recombination). Increased recombination can be beneficial for resolution of tight linkages, but may be undesirable in the construction of maps with low marker saturation.

In another embodiment, the population consists of inbred plants grouped into pedigrees according to common parents. A "pedigree structure" defines the relationship between a descendant and each ancestor that gave rise to that descendant. A pedigree structure can span one or more generations, describing relationships between the descendant and its parents, grand parents, great-grand parents, etc.

In yet another embodiment, markers can be identified or validated using an existing mapping population. For example, the mapping population described in Yu et al. (2008) Genetics 178:539-551 (herein incorporated by reference in its entirety) can be used particularly for the NAM methods. Other public or privately-held mapping populations may be suitable for the methods disclosed herein.

The methods of the present invention are applicable to essentially any population or species, particularly plant species. Preferred plants include agronomically and horticulturally important species including, for example, crops producing edible flowers such as cauliflower (Brassica oleracea), artichoke (Cynara scolvmus), and safflower (Carthamus, e.g. tinctorius); fruits such as apple (Malus, e.g. domesticus), banana (Musa, e.g. acuminata), berries (such as the currant, Ribes, e.g. rubrum), cherries (such as the sweet cherry, Prunus, e.g. avium), cucumber (Cucumis, e.g. sativus), grape (Vitis, e.g. vinifera), lemon (Citrus limon), melon (Cucumis melo), nuts (such as the walnut, Juglans, e.g. regia; peanut, Arachis hypoaeae), orange (Citrus, e.g. maxima), peach (Prunus, e.g. persica), pear (Pyra, e.g. communis), pepper (Solanum, e.g. capsicum), plum (Prunus, e.g. domestica), strawberry (Fragaria, e.g. moschata), tomato (Lycopersicon, e.g. esculentum); leafs, such as alfalfa (Medicago, e.g. sativa), sugar cane (Saccharum), cabbages (such as Brassica oleracea), endive (Cichoreum, e.g. endivia), leek (Allium, e.g. porrum), lettuce (Lactuca, e.g. sativa), spinach (Spinacia e.g. oleraceae), tobacco (Nicotiana, e.g. tabacum); roots, such as arrowroot (Maranta, e.g. arundinacea), beet (Beta, e.g. vulgaris), carrot (Daucus, e.g. carota), cassava (Manihot, e.g. esculenta), turnip (Brassica, e.g. rapa), radish (Raphanus, e.g. sativus) yam (Dioscorea, e.g. esculenta), sweet potato (Ipomoea batatas); seeds, such as bean (Phaseolus, e.g. vulgaris), pea (Pisum, e.g. sativum), soybean (Glycine, e.g. max), wheat (Triticum, e.g. aestivum), barley (Hordeum, e.g. vulgare), corn (Zea, e.g. mays), rice (Oryza, e.g. sativa); grasses, such as Miscanthus grass (Miscanthus, e.g., giganteus) and switchgrass (Panicum, e.g. virgatum); trees such as poplar (Populus, e.g. tremula), pine (Pinus); shrubs, such as cotton (e.g., Gossypium hirsutum); and tubers, such as kohlrabi (Brassica, e.g. oleraceae), potato (Solanum, e.g. tuberosum), and the like. The variety associated with any given population can be a transgenic variety, a non-transgenic variety, or any genetically modified variety. Alternatively, plants of a given species naturally occurring in the wild can also be used.

Genetic Markers

Although specific DNA sequences which encode proteins are generally well-conserved across a species, other regions of DNA (typically non-coding) tend to accumulate polymorphism, and therefore, can be variable between individuals of the same species. Such regions provide the basis for numerous molecular genetic markers.

Following generation or selection of one or more populations in the methods disclosed herein, a genotypic value for a plurality of markers is obtained for a plurality of members of the population(s). The genotypic value corresponds to the quantitative or qualitative measure of the genetic marker. The term "marker" refers to an identifiable DNA sequence which is variable (polymorphic) for different individuals within a population, and facilitates the study of inheritance of a trait or a gene. A marker at the DNA sequence level is linked to a specific chromosomal location unique to an individual's genotype and inherited in a predictable manner.

The genetic marker is typically a sequence of DNA that has a specific location on a chromosome that can be measured in a laboratory. The term "genetic marker" can also be used to refer to, e.g., a cDNA and/or an mRNA encoded by a genomic sequence, as well as to that genomic sequence. To be useful, a marker needs to have two or more alleles or variants. Markers can be either direct, that is, located within the gene or locus of interest, or indirect, that is closely linked with the gene or locus of interest (presumably due to a location which is proximate to, but not inside the gene or locus of interest). Moreover, markers can also include sequences which either do or do not modify the amino acid sequence encoded by the gene in which it is located.

In general, any differentially inherited polymorphic trait (including nucleic acid polymorphism) that segregates among progeny is a potential marker. The term "polymorphism" refers to the presence in a population of two or more allelic variants. The term "allele" or "allelic" or "marker variant" refers to variation present at a defined position within a marker or specific marker sequence; in the case of a SNP this is the actual nucleotide which is present; for a SSR, it is the number of repeat sequences; for a peptide sequence, it is the actual amino acid present; in the case of a marker haplotype, it is the combination of two or more individual marker variants in a specific combination. An "associated allele" refers to an allele at a polymorphic locus which is associated with a particular phenotype of interest. Such allelic variants include sequence variation at a single base, for example a single nucleotide polymorphism (SNP). A polymorphism can be a single nucleotide difference present at a locus, or can be an insertion or deletion of one, a few or many consecutive nucleotides. It will be recognized that while the methods of the invention are exemplified primarily by the detection of SNPs, these methods or others known in the art can similarly be used to identify other types of polymorphisms, which typically involve more than one nucleotide.

The genomic variability can be of any origin, for example, insertions, deletions, duplications, repetitive elements, point mutations, recombination events, or the presence and sequence of transposable elements. The marker may be measured directly as a DNA sequence polymorphism, such as a single nucleotide polymorphism (SNP), restriction fragment length polymorphism (RFLP) or short tandem repeat (STR), or indirectly as a DNA sequence variant, such as a single-strand conformation polymorphism (SSCP). A marker can also be a variant at the level of a DNA-derived product, such as an RNA polymorphism/abundance, a protein polymorphism or a cell metabolite polymorphism, or any other biological characteristic which has a direct relationship with the underlying DNA variant or gene product.

Two types of markers are frequently used in mapping and marker assisted breeding protocols, namely simple sequence repeat (SSR, also known as microsatellite) markers, and single nucleotide polymorphism (SNP) markers. The term SSR refers generally to any type of molecular heterogeneity that results in length variability, and most typically is a short (up to several hundred base pairs) segment of DNA that consists of multiple tandem repeats of a two or three base-pair sequence. These repeated sequences result in highly polymorphic DNA regions of variable length due to poor replication fidelity, e.g., caused by polymerase slippage. SSRs appear to be randomly dispersed through the genome and are generally flanked by conserved regions. SSR markers can also be derived from RNA sequences (in the form of a cDNA, a partial cDNA or an EST) as well as genomic material.

In one embodiment, the molecular marker is a single nucleotide polymorphism. Various techniques have been developed for the detection of SNPs, including allele specific hybridization (ASH; see, e.g., Coryell et al., (1999) Theor. Appl. Genet., 98:690-696). Additional types of molecular markers are also widely used, including but not limited to expressed sequence tags (ESTs) and SSR markers derived from EST sequences, amplified fragment length polymorphism (AFLP), randomly amplified polymorphic DNA (RAPD) and isozyme markers. A wide range of protocols are known to one of skill in the art for detecting this variability, and these protocols are frequently specific for the type of polymorphism they are designed to detect. For example, PCR amplification, single-strand conformation polymorphisms (SSCP) and self-sustained sequence replication (3 SR; see Chan and Fox, Reviews in Medical Microbiology 10:185-196).

DNA for marker analysis may be collected and screened in any convenient tissue, such as cells, seed or tissues from which new plants may be grown, or plant parts, such as leafs, stems, pollen, or cells, that can be cultured into a whole plant. In some embodiments, marker data is taken from tissues that have been associated with the trait under study. In some embodiments of the present invention, marker data is measured from multiple tissues of each plant under study. A sufficient number of cells is obtained to provide a sufficient amount of sample for analysis, although only a minimal sample size will be needed where scoring is by amplification of nucleic acids. The DNA, RNA, or protein can be isolated from the cell sample by standard nucleic acid isolation techniques known to those skilled in the art.

In one embodiment, the genotypic values correspond to the values obtained for essentially all, or all, of the SNPs of a high-density, whole genome SNP map. This approach has the advantage over traditional approaches in that, since it encompasses the whole genome, it identifies potential interactions of genomic products expressed from genes located anywhere on the genome without requiring preexisting knowledge regarding a possible interaction between the genomic products. An example of a high-density, whole genome SNP map is a map of at least about 1 SNP per 10,000 kb, at least 1 SNP per 500 kb or about 10 SNPs per 500 kb, or at least about 25 SNPs or more per 500 kb. Definitions of densities of markers may change across the genome and are determined by the degree of linkage disequilibrium within a genome region.

Additionally, a number of genetic marker screening platforms are now commercially available, and can be used to obtain the genetic marker data required for the process of the present methods. In many instances, these platforms can take the form of genetic marker testing arrays (microarrays), which allow the simultaneous testing of many thousands of genetic markers. For example, these arrays can test genetic markers in numbers of greater than 1,000, greater than 1,500, greater than 2,500, greater than 5,000, greater than 10,000, greater than 15,000, greater than 20,000, greater than 25,000, greater than 30,000, greater than 35,000, greater than 40,000, greater than 45,000, greater than 50,000 or greater than 100,000, greater than 250,000, greater than 500,000, greater than 1,000,000, greater than 5,000,000, greater than 10,000,000 or greater than 15,000,000. Examples of such a commercially available product for are those marketed by Affymetrix Inc ((www.affymetrix.com)) or Illumina (www.illumina.com). In one embodiment, the genotypic value is obtained from at least 2 genetic markers.

It will be appreciated that, due to the nature of such information, a filtering or preprocessing of the data may be required, i.e., quality control of the data. For example, marker data may be excluded according to a particular criteria (e.g., data duplication or low frequency; see, for example Zenger et. al (2007) *Anim Genet*. 38(1):7-14). Examples of such filtering are described below, although other methods of filtering the data as would be appreciated by the skilled artisan may also be employed to obtain a working data set on which the marker association is determined.

In one embodiment, marker data is excluded from the analysis where the allele frequency of a particular marker is less than about 0.01, or less than about 0.05. "Allele frequency" or "marker allele frequency" (MAF) refers to the frequency (proportion or percentage) at which an allele is present at a locus within an individual, within a line, or within a population of lines. For example, for an allele "A," diploid individuals of genotype "AA," "Aa," or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele.

In various embodiments, the set of markers evaluated for a particular trait of interest may be random markers as described above, or may be markers that have been shown or are suspected to be associated with the trait of interest in a different plant species. A large number of molecular markers for various species are known in the art and can be validated in different species using the methods disclosed herein. For example, a group of candidate genes that has been identified based on their molecular functions and/or performances in corn may be tested in soybean. Thus, the models described herein are useful for validating the effects of these candidate genes in a different plant species. When evaluating a set of candidate markers, generally random markers having no known association will also be included in the analysis.

Trait of Interest

The methods of the present invention are applicable to any phenotype with an underlying genetic component, i.e., any heritable trait. A "trait" is a characteristic of an organism which manifests itself in a phenotype, and refers to a biological, performance or any other measurable characteristic(s), which can be any entity which can be quantified in, or from, a biological sample or organism, which can then be used either alone or in combination with one or more other quantified entities. A "phenotype" is an outward appearance or other visible characteristic of an organism and refers to one or more trait of an organism.

Many different traits can be inferred by the methods disclosed herein. The phenotype can be observable to the naked eye, or by any other means of evaluation known in the art, e.g., microscopy, biochemical analysis, genomic analysis, an assay for a particular disease resistance, etc. In some cases, a phenotype is directly controlled by a single gene or genetic locus, i.e., a "single gene trait." In other cases, a phenotype is the result of several genes. A "quantitative trait loci" (QTL) is a genetic domain that is polymorphic and effects a phenotype that can be described in quantitative terms, e.g., height, weight, oil content, days to germination, disease resistance, etc, and, therefore, can be assigned a "phenotypic value" which corresponds to a quantitative value for the phenotypic trait.

For any trait, a "relatively high" characteristic indicates greater than average, and a "relatively low" characteristic indicates less than average. For example "relatively high yield" indicates more abundant plant yield than average yield for a particular plant population. Conversely, "relatively low yield" indicates less abundant yield than average yield for a particular plant population.

In the context of an exemplary plant breeding program, quantitative phenotypes include, yield (e.g., grain yield, silage yield), stress (e.g., mid-season stress, terminal stress, moisture stress, heat stress, etc.) resistance, disease resistance, insect resistance, resistance to density, kernel number, kernel size, ear size, ear number, pod number, number of seeds per pod, maturity, time to flower, heat units to flower, days to flower, root lodging resistance, stalk lodging resistance, ear height, grain moisture content, test weight, starch content, grain composition, starch composition, oil composition, protein composition, nutraceutical content, and the like.

In addition, the following phenotypic values may be correlated with the marker of interest: color, size, shape, skin thickness, pulp density, pigment content, oil deposits, protein content, enzyme activity, lipid content, sugar and starch content, chlorophyll content, minerals, salt content, pungency, aroma and flavor and such other features. For each of these indices, a distribution of parameters is determined for the sample by determining a feature (e.g., weight) associated with each item in the sample, and then measuring mean and standard deviation values from the distribution.

Similarly, the methods are equally applicable to traits which are continuously variable, such as grain yield, height, oil content, response to stress (e.g., terminal or mid-season stress) and the like, or to meristic traits that are multi-categorical, but can be analyzed as if they were continuously variable, such as days to germination, days to flowering or fruiting, and to traits with are distributed in a non-continuous (discontinuous) or discrete manner. However, it is to be understood that analogous or other unique traits may be characterized using the methods described herein, within any organism of interest.

In addition to phenotypes directly assessable by the naked eye, with or without the assistance of one or more manual or automated devices, included, e.g., microscopes, scales, rulers, calipers, etc., many phenotypes can be assessed using biochemical and/or molecular means. For example, oil content, starch content, protein content, nutraceutical content, as well as their constituent components can be assessed, optionally following one or more separation or purification step, using one or more chemical or biochemical assay. Molecular phenotypes, such as metabolite profiles or expression profiles, either at the protein or RNA level, are also amenable to evaluation according to the methods of the present invention. For example, metabolite profiles, whether small molecule metabolites or large bio-molecules produced by a metabolic pathway, supply valuable information regarding phenotypes of agronomic interest. Such metabolite profiles can be evaluated as direct or indirect measures of a phenotype of interest. Similarly, expression profiles can serve as indirect measures of a phenotype, or can themselves serve directly as the phenotype subject to analysis for purposes of marker correlation. Expression profiles are frequently evaluated at the level of RNA expression products, e.g., in an array format, but may also be evaluated at the protein level using antibodies or other binding proteins.

In addition, in some circumstances it is desirable to employ a mathematical relationship between phenotypic attributes rather than correlating marker information independently with multiple phenotypes of interest. For example, the ultimate goal of a breeding program may be to obtain crop plants which produce high yield under low water, i.e., drought, conditions. Rather than independently correlating marker for yield and resistance to low water conditions, a mathematical indicator of the yield and stability of yield over water conditions can be correlated with markers. Such a mathematical indicator can take on forms including; a statistically derived index value based on weighted contributions of values from a number of individual traits, or a variable that is a component of a crop growth and development model or an ecophysiological model (referred to collectively as crop growth models) of plant trait responses across multiple environmental conditions. These crop growth models are known in the art and have been used to study the effects of genetic variation for plant traits and map QTL for plant trait responses. See references by Hammer et al. 2002. European Journal of Agronomy 18: 15-31, Chapman et al. 2003. Agronomy Journal 95: 99-113, and Reymond et al. 2003. Plant Physiology 131: 664-675.

Association Analysis

The methods disclosed herein involved comparison of positively-associated markers identified or validated by multiple linkage analysis strategies. In various embodiments, markers are tested using genome-wide association (GWA) mapping strategies. Positively-correlated markers are aligned on a physical genetic map of the species being tested. Positively-correlated markers identified or validated using other methods, such as eQTL analysis or NAM are also aligned on the physical map. Candidate markers are selected for further use if the markers are identified or validated using GWA and one or both of eQTL or NAM.

Genetics data have been used in the field of trait analysis in order to attempt to identify the genes that affect such traits. A key development in such pursuits has been the development of large collections of molecular/genetic markers, which can be used to construct detailed genetic maps of species. These maps are used in Quantitative Trait Locus (QTL) mapping methodologies such as single-marker mapping, interval mapping, composite interval mapping and multiple trait mapping. QTL mapping methodologies provide statistical analysis of the association between phenotypes and genotypes for the purpose of understanding and dissecting the regions of a genome that affect traits.

Association mapping makes use of markers within candidate genes, which are genes that are thought to be functionally involved in development of the trait because of information such as biochemistry, physiology, transcriptional profiling and reverse genetic experiments in model organisms. In the simplest definition, association mapping is the utility of linkage disequilibrium, also known as gametic phase disequilibrium, in natural populations to identify markers with significant allele frequency differences between individuals with the trait of interest and individuals not exhibiting the trait of interest. Genome-wide association analysis (GWA) is an approach that involves rapidly scanning markers across the complete (or near complete) sets of DNA, or genomes, of organisms of the population to find genetic variations associated with a particular trait. A statistical association between genotypes at a marker locus and the trait of interest is considered to be evidence of close physical linkage between the marker and the QTL controlling that trait (Pritchard et al., 2000).

While classical gene mapping approaches are useful in genome-wide scan for loci controlling QTLs, association mapping is emerging as a leading tool for precise estimation of QTL positions. For example, this method has been used to identify genes for complex traits in medical genetics (Lander and Schork, 1994; Risch, 2000), and its application is gradually moving to other fields such as plant genetics. Since association mapping uses natural populations, many generations (and therefore meioses) have elapsed, thus recombination will have removed association between a QTL and any marker not tightly linked to it. Association mapping thus allows for much finer mapping than standard bi-parental cross approaches. Marker data at regular intervals across the genome under study or in gene regions of interest is used to monitor segregation or detect associations in a population of interest. In some embodiments, these regularly defined intervals are defined in Morgans or, more typically, centimorgans (cM). A Morgan is a unit that expresses the genetic distance between markers on a chromosome. A Morgan is defined as the distance on a chromosome in which one recombination event is expected to occur per gamete per generation. In some embodiments, each regularly defined interval is less than 100 cM. In other embodiments, each regularly defined interval is less than 10 cM, less than 5 cM, less than 2.5 cM, less than 2 cM, less than 1.5 cM, or less than 1 cM.

Linkage Models for Genome-Wide Association

The objective of genetic mapping is to identify simply inherited markers in close proximity to genetic factors affecting quantitative traits, that is, QTL. This localization relies on processes that create a statistical association between marker and QTL alleles and processes that selectively reduce that association as a function of the marker distance from the QTL. Several types of known statistical analyses can be used to infer marker/trait association from the phenotype/genotype data, but a basic idea is to detect markers, i.e., polymorphisms, for which alternative genotypes have significantly different average phenotypes. For example, if a given marker locus A has three alternative genotypes (AA, Aa and aa), and if those three classes of individuals have significantly different phenotypes, then one infers that locus A is associated with the trait. The significance of differences in phenotype may be tested by several types of standard statistical tests such as linear regression of marker genotypes on phenotype or analysis of variance (ANOVA). The genetic map is created by placing genetic markers in genetic (linear) map order so that the positional relationships between markers are understood.

Many known programs can be used to perform association analyses in accordance with this aspect of the invention. One such program is MapMaker/QTL, which is the companion program to MapMaker and is the original QTL mapping software. MapMaker/QTL analyzes marker data using standard interval mapping. Another such program is QTL Cartographer, which performs single-marker regression, interval mapping (Lander and Botstein, Id.), multiple interval mapping and composite interval mapping (Zeng, 1993, PNAS 90: 10972-10976; and Zeng, 1994, Genetics 136: 1457-1468). QTL Cartographer permits analysis from $F_2$ or backcross populations. QTL Cartographer is available from statgen.ncsu.edu/qtlcart/cartographer (North Carolina State University). Another program that can be used is Qgene, which performs QTL mapping by either single-marker regression or interval regression (Martinez and Curnow 1994 Heredity 73:198-206). Using Qgene, multiple different population types (all derived from inbreeding) can be analyzed. Qgene is available from qgene.org. Yet another program is MapQTL, which conducts standard interval mapping (Lander and Botstein, Id.), multiple QTL mapping (MQM) (Jansen, 1993, Genetics 135: 205-211; Jansen, 1994, Genetics 138: 871-881), and nonparametric mapping (Kruskal-Wallis rank sum test). MapQTL can analyze a variety of pedigree types including outbred pedigrees (cross pollinators). MapQTL is available from Plant Research International, Plant Research International, P.O. Box 16, 6700 AA Wageningen, The Netherlands; plant.wageningen-ur.nl/default.asp?section=products). Yet another program that may be used in some embodiments is Map Manager QT, which is a QTL mapping program (Manly and Olson, 1999, Mamm Genome 10: 327-334). Map Manager QT conducts single-marker regression analysis, regression-based simple interval mapping (Haley and Knott, 1992, Heredity 69, 315-324), composite interval mapping (Zeng 1993, PNAS 90: 10972-10976), and permutation tests. A description of Map Manager QT is provided by the reference Manly and Olson, 1999, *Mammalian Genome* 10: 327-334.

Yet another program that may be used to perform linkage analysis is MultiCross QTL, which maps QTL from crosses originating from inbred lines. MultiCross QTL uses a linear regression-model approach and handles different methods such as interval mapping, all-marker mapping, and multiple QTL mapping with cofactors. The program can handle a wide variety of simple mapping populations for inbred and outbred species. MultiCross QTL is available from Unite de Biometrie et Intelligence Artificielle, IRA, 31326 Castanet Tolosan, France.

Still another program that can be used to perform linkage analysis is QTL Cafe. The program can analyze most populations derived from pure line crosses such as $F_2$ crosses, backcrosses, recombinant inbred lines, and doubled haploid lines. QTL Cafe incorporates a Java implementation of Haley & Knotts' flanking marker regression as well as Marker regression, and can handle multiple QTLs. The program allows three types of QTL analysis single marker ANOVA, marker regression (Kearsey and Hyne, 1994, Theor. Appl. Genet., 89: 698-702), and interval mapping by regression, (Haley and Knott, 1992, Heredity 69: 315-324). QTL Cafe is available from web.bham.ac.uk/g.g.seaton/.

Yet another program that can be used to perform linkage analysis is MAPL, which performs QTL analysis by either interval mapping (Hayashi and Ukai, 1994, Theor. Appl. Genet. 87:1021-1027) or analysis of variance. Different population types including $F_2$, backcross, recombinant inbreds derived from $F_2$ or backcross after a given generations of selfing can be analyzed. Automatic grouping and ordering of numerous markers by metric multidimensional scaling is possible. MAPL is available from the Institute of Statistical Genetics on Internet (ISGI), Yasuo, UKAI, web.bham.ac.uk g.g.seaton/.

Another program that can be used for linkage analysis is R/qtl. This program provides an interactive environment for mapping QTLs in experimental crosses. R/qtl makes uses of the hidden Markov model (HMM) technology for dealing with missing genotype data. R/qtl has implemented many HMM algorithms, with allowance for the presence of genotyping errors, for backcrosses, intercrosses, and phase-known four-way crosses. R/qtl includes facilities for estimating genetic maps, identifying genotyping errors, and performing single-QTL genome scans and two-QTL, two-dimensional genome scans, by interval mapping with Haley-Knott regression, and multiple imputation. R/qtl available from Karl W. Broman, Johns Hopkins University, biosun01. biostatjh-sph.edu/.about.kbroman/qtl/.

The java-based software TASSEL (Trait Analysis by aSSociation, Evolution and Linkage) can be used to determine marker: trait associations. See, Yu et al. (2005) *Nature Genetics* 38:203-208, herein incorporated by reference. TASSEL allows for linkage disequilibrium statistics to be calculated and visualized graphically. TASSEL is capable of merging data from different sources into a single analysis data set, impute missing data using a k-nearest-neighbor algorithm (Cover and Hart (1967) *Proc IEEE Trans Inform Theory* 13), and conduct principal components analysis (PCA) to reduce a set of correlated phenotypes. Open source code for the TASSEL software package is available at: sourceforge.net/projects/tassel.

TASSEL can be used with the Quantitative Inbred Pedigree Disequilibrium Test (QIPDT). QIPDT is a test for family based association mapping with inbred lines from plant breeding programs. See Stich et al. (2006) *Theor Appl Genet* 113:1121-1130; herein incorporated by reference. QIPDT is a QTL detection method for data collected routinely in plant breeding programs. QIPDT is a family-based association test applicable to genotypic information of parental inbred lines and geno- and phenotypic information of their offspring inbreds. The QIPDT extends the QPDT, a family-based association test. Nuclear families consisting of two parental inbred lines and at least one offspring inbred line can be combined to extended pedigrees, the basis of the QIPDT, if the parental lines of different nuclear families are related. QIPDT also takes into account the correction of Martin et al. (2001) *Am J Hum Genet* 68:1065-1067 regarding the pedigree disequilibrium test.

The improved regression model QIPDT2 can also be used. QIPDT2 adopts the same methods for marker coding and phenotypic adjustment as used in QIPDT 1, with two improvements: 1) a regression model is fitted for the marker and phenotypic data, which allows estimation of genetic effects and phenotypic contributions for markers in question; 2) extending the approach to hybrids of inbreds with different testers grown at multiple locations, while the original approach is applicable for inbreds only. Such extension is achieved by extracting genetic values of inbreds from a mixed model that accounts for tester effects and non-genetic effects (e.g. locations). QIPDT2 is described in U.S. patent application Ser. No. 12/328,689, filed Dec. 4, 2008.

Additional commercially available statistical software packages commonly used to do this type of analysis include SAS Enterprise Miner (SAS Institute Inc., Cary, N.C.) and Splus (Insightful Corporation. Cambridge, Mass.). Those of skill in the art will appreciate that there are several other programs and algorithms that can be used in the steps of the methods of the present invention where quantitative genetic analysis is needed, and all such programs and algorithms are within the scope of the present invention.

Nested Association Mapping

In various embodiments, candidate markers are identified or validated by comparing positively-correlated markers identified using GWA with positively-correlated markers using nested association mapping (NAM) and selecting for further use any marker shown to be positively correlated using both methods. The NAM strategy addresses complex trait dissection at a fundamental level through generating a common mapping resource that enables researchers to efficiently exploit genetic, genomic, and systems biology tools.

Building on the genetic principles in previous genomic mapping strategies and methods (Meuwissen et al. 2002 *Genetics* 161: 373-379; Mott and Flint 2002, *Genetics* 160: 1609-1618; Darvasi and Shifman 2005, *Nat. Genet.* 37:118-119), NAM has the advantages of lower sensitivity to genetic heterogeneity and higher power as well as higher efficiency in using the genome sequence or dense markers while still maintaining high allele richness due to diverse founders. NAM creates an integrated mapping population specifically designed for a full genome scan with high power for quantitative trait loci (QTL) with effects of different sizes.

The procedure in NAM involves first selecting diverse founders and developing a large set of related mapping progenies. In various embodiments, the related progenies consists of a set of recombinant inbred lines (RIL) derived from a cross between a single common parent and a set of diverse founder lines. The RILs are developed by multiple rounds of selfing. The genetic background effect of these parental founders on mapping individual QTL is systematically minimized by reshuffling the genomes of the two parents of each cross during RIL development as well as by the combined analysis of all RILs across multiple crosses. In general, the strategy of projecting sequence information, nested within informative markers, from the most connected individuals to the remaining individuals is applicable to a wide range of species, including humans, mice, *Arabidopsis,* and rice.

Next the founder lines are either sequenced completely or densely genotyped, and a smaller number of tagging markers on both the founders and the progenies are genotyped to define the inheritance of chromosome segments and to project the high-density marker information from the founders to the progenies. The progenies are phenotyped for various traits, and genome-wide association analysis is conducted to relate phenotypic traits with projected high-density markers of the progenies. See, Yu et al. 2008, Genetics 178: 539-551.

As in general association mapping, the mapping resolution offered by NAM largely depends on the linkage disequilibrium among the founder individuals. Empirical studies with maize candidate genes sequenced across diverse lines have shown a rapid decay of LD over 2000 bp (Wilson et al. 2004, Plant Cell 16: 2719-2733). Recent genome-wide analysis in diverse accessions of *Arabidopsis* (Nordborg et al. 2005, *PLoS Biol.* 3:e196) and breeds of dog (*Canis familiaris*) (Lindblad-Toh et al. 2005, *Nature* 438: 803-819) agreed with this pattern: LD decays rapidly across genetically diverse germplasm. With the NAM strategy, this advantage in resolution is fully utilized without the coupled drawback-the need for good candidate genes or a large number of markers-by projecting the genomic information from the founders to the RILs.

Models for NAM

In various embodiments of the present invention, the NAM strategy for identifying or validating candidate markers employs regression models for detecting an association between a trait of interest and a marker. In statistics, regression analysis is a collective name for techniques for the modeling and analysis of numerical data consisting of values of a dependent variable (response variable) and of one or more independent variables (explanatory variables). The dependent variable in the regression equation is modeled as a function of the independent variables, corresponding parameters ("constants"), and an error term. The error term is treated as a random variable. It represents unexplained variation in the dependent variable. The parameters are estimated so as to give a "best fit" of the data. Most commonly the best fit is evaluated by using the least squares method, but other criteria have also been used.

Least squares can be interpreted as a method of fitting data. The best fit in the least-squares sense is that instance of the model for which the sum of squared residuals has its least value, a residual being the difference between an observed value and the value given by the model. Least squares corresponds to the maximum likelihood criterion if the experimental errors have a normal distribution and can also be derived as a method of moments estimator. Regression analysis is available in most statistical software packages.

For the purposes of the present invention, any suitable regression method can be used to identify QTL in a nested population. Exemplary regression models are described herein. Further provided are two novel regression models (SMR and MMR) that can be used to identify, validate, or prioritize for downstream use a marker associated with a trait of interest.

Single Marker Regression (SMR)

Provided herein is a novel single marker regression (SMR) tool for performing nested association mapping. The method is similar to single-marker regression used in standard QTL linkage analysis, with two key modifications. One is that the polygenetic background information is incorporated from each subpopulation into the model. In doing so, the genetic variation caused by different genetic backgrounds may be separated from the model, thus improving QTL mapping power. At the same time, the inclusion of genetic background information eliminates the effect of population stratification on QTL mapping, minimizing false positive discovery rates. The second improvement over existing methods is exclusion of marker data from distorted populations. This feature allows the model to avoid the influence of marker segregation distortion on QTL detection, which may create challenges in association mapping. This model is further benefited by the experimental design of NAM, which is a combination of linkage and association mapping. The present invention uses a unique linear model to describe the relationship between trait values and marker genotypes may be written as:

$$y_{ij} = \mu + x_{ij}a + g_i u_i + e_{ij}$$

where $y_{ij}$ is the phenotypic value of the individual j in the subpopulation i; $\mu$ is the overall mean; a is the additive effect of QTL; $g_i$ is the indicator variable of the subpopulation i; $u_i$ is the effect of the subpopulation i; $e_{ij}$ is the residual error which is assumed to follow a normal distribution with mean zeros and variance $\sigma^2$. According to the present invention, the genotype $x_{ij}$, is defined as 1 if the individual j carries the allele from the common parent and −1 if the individual j carries the allele from the other parent. This definition is based on there being only two distinct alleles for each marker. To exploit the simplicity of regression, the genetic background effect $u_i$ is assumed to be a fixed effect. As used herein the term "fixed effects" preferably refers seasonal, spatial, geographic, environmental or managerial influences that cause a systematic effect on the phenotype or to those effects with levels that were deliberately arranged by the experimenter, or the effect of a gene or marker that is consistent across the population being evaluated. Thus, the invention includes the genetic background effect $u_i$ into the model to account for the influence from population stratification, and therefore reduce the residual variance.

This SMR method differs from the original marker-based regression method for NAM (Yu et al (2006) *Nature Genetics* 38(2):203-208) in the use of polymorphic markers. From NAM marker data, it is easily seen that some markers show polymorphism in some subpopulations, but not in others. In this case, the inclusion of noninformative markers may lead to segregation distortion of marker genotypes at that locus, and the distortion could cause the reduction of QTL mapping efficiency, power and precision. To avoid the problem, the present invention uses a marker-filtered procedure incorporated into the SMR model to reduce the potential risk due to marker distortion. This marker-filtered procedure means that only the phenotypic and genotypic data from those subpopulations with segregated genotypes of a marker are included in each analysis. Thus, in various embodiments of the invention, the subpopulations with noninformative genotypes are excluded prior to SMR analysis. The procedure enables SMR to identify those alleles with very low frequency (less than 5%) in NAM.

Composite Interval Mapping

When multiple linked QTLs are present, current single marker and interval methods often place QTLs in the wrong location, for example generating a ghost QTL in the position between the two real QTLs. One approach for dealing with multiple QTLs is to modify standard interval mapping to include additional markers as cofactors (also referred to herein as "covariates") in the analysis. Generally, the use of cofactors reduces the bias and sampling error of the estimated QTL positions (Utz and Melchinger, Biometrics in Plant Breeding, Proceedings of the Ninth Meeting of the Eucarpia Section Biometrics in Plant Breeding, The Netherlands, 1994). Using the appropriate unlinked markers can partly account for the segregation variance generated by unlinked QTLs, while the effects of linked QTLs can be reduced by including markers linked to the interval of interest. This general approach of adding marker cofactors to an otherwise standard interval analysis, often referred to as "composite interval mapping" or CIM, results in substantial increases in power to detect a QTL and in the precision of estimates of QTL position.

CIM handles multiple QTLs by incorporating multilocus marker information from organisms by modifying standard interval mapping to include additional markers as cofactors for analysis. In these methods, one performs interval mapping using a subset of marker loci as covariates. These markers serve as proxies for other QTLs to increase the resolution of interval mapping, by accounting for linked QTLs and reducing the residual variation. Exemplary CIM models are described in, for example, Jansen, 1993, Genetics 135, p. 205; Zeng, 1994, Genetics 136, p. 1457, each of which is herein incorporated by reference in its entirety.

Additional models can be used. Many modifications and alternative approaches to interval mapping have been reported, including the use non-parametric methods (Kiruglyak and Lander, Genetics, 121:1421-1428, 1995). Multiple regression methods or models can be also be used, in which the trait is regressed on a large number of markers (Jansen et al., Theor. Appl. Genet., 91:33-37, 1995; Weber and Wricke, Advances in Plant Breeding, Blackwell, 1994).

Multiple Marker Regression (MMR)

To account for the influences from other QTLs, a novel multiple marker regression (MMR) method is described herein. This method uses cofactor markers to absorb the effect of other QTLs. The linear model for MMR is:

$$y_{ij} = \mu + x_{ij}a + \Sigma(k=1,m)c_{ijk}b_k + g_i u_i + e_{ij}$$

where $y_{ij}$ is the phenotypic value of the individual j in the subpopulation i; $\mu$ is the overall mean; $x_{ij}$ is the genotype of QTL; a is the additive effect of QTL; $c_{ijk}$ is the cofactor marker k for the individual j in the subpopulation i, and $b_k$ is the effect of the cofactor marker k; $g_i$ is the indicator variable of the subpopulation i; $u_i$ is the effect of the subpopulation i, and $e_{ij}$ is the residual error which is assumed to follow a normal distribution with mean zeros and variance $\sigma^2$. This MMR model is similar to composite interval mapping (Zeng 1993, 1994, infra).

The key problem with CIM has been the choice of suitable marker loci to serve as covariates; once these have been chosen, CIM turns the model selection problem into a single-dimensional scan. Prior to the present invention, the choice of marker cofactors has not been solved. In the present invention, stepwise regression is used to select cofactor markers based on the significance level 0.01. The linear model used to choose cofactors is:

$$y_{ij} = \mu + x_{ij}a + c_{ijk}b_k + g_i u_i + e_{ij}.$$

This stepwise regression model is different from the one used for conventional composite interval mapping (Zeng 1993, 1994) and the one originally used for NAM (Yu et al 2008). In the present MMR model, stepwise regression is used for a NAM population with the inclusion of genetic backgrounds from different subpopulations into the model. This method of selection is focused on selecting those QTLs which have stable effects across multiple subpopulations. Thus, it effectively reduces the number of cofactors included in the model, avoiding the problem of over saturation.

With cofactor markers, it is possible to obtain much clearer LOD profile from MMR than SMR. The use of cofactor markers is to reduce the residual error, and therefore increase the significance of the QTL hypothesis test. The novel MMR model provided herein shows the ability to separate closely linked QTL and to locate a QTL within a narrow genomic region. In various embodiments, all genotypic data from all the subpopulations are used for data analysis.

It is expected that SMR and MMR will provide similar results for those markers with no distorted segregation, while they may show differences in markers with skewed genotypic segregation. Thus, in some embodiments, both SMR and MMR are performed as a complement combination for the NAM dataset. SMR and MMR can be performed separately for the same set of trait phenotypic data and marker data. Then, the results obtained from each method can be compared. For those QTL not consistently identified by both SMR and MMR, marker segregation analysis can be performed. This analysis can be performed to determine if the inconsistency of those QTL is caused by marker distortion. Distortion of the marker genotype can result in missing true QTL (false negative), or it can result in detection of false QTL if the marker genotype happens to correlate with the trend of the trait. For those QTL consistently identified by SMR and MMR, marker segregation analysis may not be necessary. However, joint use of SMR and MMR under any circumstance is likely to result in QTL with improved power and decreased false positive rate. Thus, in this aspect of the invention, positively-correlated markers identified by both SMR and MMR are considered.

Testing QTL Effect

Often the goal of an association study is not simply to detect marker/trait associations, but to estimate the location of genes affecting the trait directly (i.e., QTLs) relative to the marker locations. In a simple approach to this goal, one makes a comparison among marker loci of the magnitude of difference among alternative genotypes or the level of significance of that difference. Trait genes are inferred to be located nearest the marker(s) that have the greatest associated genotypic difference. In a more complex analysis, such as interval mapping (Lander and Botstein, Genetics 121:185-199, 1989), each of many positions along the genetic map (for example, at 1 cM intervals) is tested for the likelihood that a QTL is located at that position. The genotype/phenotype data are used to calculate for each test position a LOD score (log of likelihood ratio). When the LOD score exceeds a critical threshold value, there is significant evidence for the location of a QTL at that position on the genetic map (which will fall between two particular marker loci).

The hypotheses to test QTL effect can be formulated as $H_0$: a=0 and $H_1$: $a_1 \neq 0$. The parameters under $H_0$ or $H_1$ are estimated by the least squares method based on the regression model depending on whether or not QTL effect is included in the model. Then the likelihood ratio (LR) can be obtained. The likelihood ratio is the ratio of the maximum probability of a result under two different hypotheses. A likelihood-ratio test is a statistical test for making a decision between two hypotheses based on the value of this ratio. Being a function of the data x, the LR is therefore a statistic. The likelihood-ratio test rejects the null hypothesis if the value of this statistic is too small. How small is too small depends on the significance level of the test, i.e., on what probability of Type I error is considered tolerable ("Type I" errors consist of the rejection of a null hypothesis that is true).

Lower values of the likelihood ratio mean that the observed result is less likely to occur under the null hypothesis. Higher values mean that the observed result is more likely to occur under the null hypothesis. The LR can be obtained from the regression models as LR=$-2(l_{reduced} - l_{full})$, where $l_{reduced}$ is the log likelihood of the reduced model, corresponding to $H_0$, and $l_{full}$ is that of the full model, corresponding to $H_1$ (Lander and Botstein 1989).

From the LR, a logarithm of the odds (LOD) score is calculated. A LOD score is a statistical estimate of whether two loci are likely to lie near each other on a chromosome and are therefore likely to be genetically linked. In the present case, a LOD score is a statistical estimate of whether a given position in the genome under study is linked to the quantitative trait corresponding to a given gene. In one embodiment, the LOD score is calculated as LR/(2 ln 10). The LOD score essentially indicates how much more likely the data are to have arisen assuming the presence of a QTL versus in its absence. The LOD threshold value for avoiding a false positive with a given confidence, say 95%, depends on the number of markers and the length of the genome. Graphs indicating LOD thresholds are set forth in Lander and Botstein, Genetics, 121:185-199 (1989), and further described by Ars and Moreno-Gonzalez, Plant Breeding, Hayward, Bosemark, Romagosa (eds.) Chapman & Hall, London, pp. 314-331 (1993).

Generally, a LOD score of three or more suggests that two loci are genetically linked, a LOD score of 4 or more is strong evidence that two loci are genetically linked, and a LOD score of 5 or more is very strong evidence that two loci are genetically linked. However, the significance of any given LOD score actually varies from species to species depending on the model used.

Permutation Tests for NAM

The original multiple regression method for NAM (Yu et al 2008) used a very low significance level $10^{-7}$ as a threshold for QTL detection. This method is not appropriate for determining LOD threshold at a given significance level, especially based on a dense linkage map. To solve this problem, the present invention provides a novel method of permutation testing to determine the empirical LOD threshold at the given significance level 0.05 and 0.01. The permutation method of the invention reshuffles the phenotypic values within each subpopulation without destroying the structure of subpopulations and the correlation between different traits of interest. To accomplish this, SMR and MMR are performed on the randomized phenotypic data and original marker data, and then the maximum LOD score is calculated across all markers in the genome. This kind of analysis is repeated 1000 times, and the maximum LOD score from each analysis is recorded. Finally, these LOD scores are sorted in ascending order. The LOD value at the position $(1-\alpha)*n$ is the empirical LOD threshold at the significance level $\alpha$. In some embodiments, the 0.01 threshold may not be stable due to limited number of permutation tests. Thus, 10000 permutations are recommended at this significance level. However, it is understood that a different number of permutations is possible and still obtain the desired significance level. For example, about 2000, about 3000, about 4000, about 5000, about 6000, about 7000, about 8000, about 9000, or more permutations can be performed.

Expression QTL Analysis

Another approach encompassed by the present invention for prioritizing candidate genes for downstream applications is the combination of GWA and DGE (Digital Gene Expression) techniques to further prioritize genes for implementation or validation through resolution of eQTL. Certain marker discovery/genotyping platforms are designed in such a way as to provide sufficient markers for GWA along with the Expression Profile of each genotyped marker (e.g., the Solexa SNP discovery/genotyping platform). Thus, classical QTL analyses are combined with gene expression profiling i.e. by DNA microarrays. Such expression QTLs (e-QTLs) describe cis- and trans-controlling elements for the expression of genes associated with a trait of interest. These methods are capable of determining the relationship between markers on the linkage map and the expression of the one or more markers to identify statistically significant QTLs. Expression can be monitored and correlated with the trait of interest under a variety of conditions, such as development stage, environmental exposure, and the like. Such a relationship may be determined using any association method described herein or known to one of skill in the art, for example, but not limited to, single point ANOVAs, simple regression, Interval mapping, composite interval mapping, and NAM.

Thus, eQTL analysis begins with gene expression data (e.g., from a gene expression study or a proteomics study) and genotype data from a population under study. In one aspect of the present invention, the expression level of a gene in an organism in the population of interest is determined by measuring an amount of at least one cellular constituent that corresponds to the gene in one or more cells of the organism. As used herein, the term "cellular constituent" comprises individual genes, proteins, mRNA expressing a gene, and/or any other variable cellular component or protein activity, degree of protein modification (e.g., phosphorylation), for example, that is typically measured in a biological experiment by those skilled in the art.

The expression level of a nucleotide sequence in a gene can be measured by any high throughput techniques. However measured, the result is either the absolute or relative amounts of transcripts or response data, including but not limited to values representing abundances or abundance ratios. Measurement of the expression profile may be made by hybridization to transcript arrays (e.g., "transcript arrays" or "profiling arrays"). Transcript arrays can be employed for analyzing the expression profile in a cell sample and especially for measuring the expression profile of a cell sample of a particular tissue type or developmental stage or a cell type exposed to a particular environmental condition.

The expression data is transformed into an expression statistic that is used to treat each cellular constituent abundance in gene expression data as a quantitative trait. Then, for each gene in a plurality of genes expressed by an organism in the population, a quantitative trait locus (QTL) analysis is performed using the genetic marker map in order to produce QTL data. A set of expression statistics represents the quantitative trait used in each QTL analysis.

The expression statistics commonly used as quantitative traits in the analyses include, but are not limited to the mean log ratio, log intensity, and background-corrected intensity. Other types of expression statistics may also be used as quantitative traits. For example, transformation may be performed using a normalization module. In such embodiments, the expression level of a plurality of genes in each organism under study is normalized. Any normalization routine may be used. Representative normalization routines include, but are not limited to, Z-score of intensity, median intensity, log median intensity, Z-score standard deviation log of intensity, Z-score mean absolute deviation of log intensity calibration DNA gene set, user normalization gene set, ratio median intensity correction, and intensity background correction. Furthermore, combinations of normalization routines may be run.

Within the past decade, several technologies have made it possible to monitor the expression level of a large number of transcripts at any one time (see, e.g., Schena et al., 1995, Science 270:467-470; Lockhart et al., 1996, Nature Biotechnology 14:1675-1680; Blanchard et al., 1996, Nature Biotechnology 14, 1649; U.S. Pat. No. 5,569,588). For example, expression may be measured using Digital Gene Expression (DGE). DGE provides a hypothesis free, global, and quantitative analysis of the entire transcriptome. This application analyzes the level of expression of virtually all genes in a sample by counting the number of individual mRNA molecules produced from each gene. There is no requirement that genes be identified and characterized prior to conducting an experiment. DGE platforms are commercially available, for example, through Helicos Biosciences (Cambridge, Mass.) and Illumina, Inc. (San Diego, Calif.).

The ability to perform genome-wide single nucleotide polymorphism (SNP) analysis has made possible GWA studies for the identification of common trait variants. Whole-genome studies of the epigenome, or nonsequence-based information inherited during cell division, has lagged behind. Part of the reason is the diverse nature of epigenetic control elements, such as DNA methylation and multiple chromatin modifications. Standard array-based allele-indiscriminate gene expression analysis may reveal epigenetic changes at individual genes, or may simply reflect dynamic changes in gene expression mediated by trans-acting regulatory components such as transcription factors. The ability to discriminate allele-specific expression (ASE) of the two alleles of genes can reveal changes in epigenetic control, since the two alleles are affected by the same transcription factors, yet would differ in cis-acting control elements.

Thus, eQTL analysis encompasses evaluation of allele-specific expression. In principal, standard QTL or Marker Association methods link a discreet segment of DNA, such as a haplotype, to a percentage of phenotypic variance at some level of significance. Usually the phenotype is a quantifiable measure of plant performance such as yield. Likewise, an eQTL analysis considers gene expression a quantifiable phenotype that can be associated with a discreet segment of DNA. Such methods are used to link specific expression patterns to a specific location on the genome but fail to account for cis/trans acting sequences or epigenetic influences on gene expression.

Encompassed herein is a method by which the quantifiable expression of each gene of each individual of a defined population is sub-divided into expression value ranges based on haplotype. For example, if Gene ABC has 8 haplotypes, then each haplotype is assigned an expression range based on the collective expression of each haplotype across each individual of the population. Subsequent association analyses can then be performed between the haplotype expression and both the sequence haplotype and quantifiable phenotype.

In general terms, the results of this type of analysis reveal one of three patterns: (1) each haplotype of a single gene has its own unique expression range, which may indicate cis-acting allele specific gene expression; (2) each haplotype of a single gene has the same expression range, which may indicate conserved regulation of the gene in question; or, (3) a specific haplotype of a single gene has multiple expression ranges, which may indicate trans-acting allele specific expression or epigenetic regulation.

In some instances, this type of analysis may provide independent confirmation of an association of a gene haplotype with a trait of interest. For example, if a specific haplotype associates with increased yield and a specific expression value of the same haplotype also associates with increased yield, there is a stronger indication that the haplotype is associated with the trait of interest.

Alternatively, or in addition, this analysis may facilitate identification and association of epigenetic or cis/trans allele specific influences over a trait of interest. For example, under normal conditions, each unique haplotype of a single gene has the same expression range. In such cases, any association of a specific haplotype to a specific value of the trait of interest (e.g., increased yield in a plant) may be attributed to DNA variation at that locus. Alternatively, each haplotype could have its own unique expression range(s). In such cases, association of a specific haplotype and expression range alone or in combination with increased yield could be attributed to epigenetic or cis/trans allele specific influences over plant yield.

Methods for examining ASE are described in, for example, Lo et al. (2003) *Genome Res.* 13(8):1855-62; Pant et al. (2006) *Genome Res.* 16(3):331-9; and, Bjornsson et al. (2008) *Genome Research* 18:771-779, each of which is herein incorporated by reference in its entirety).

Downstream Use of Markers

The markers identified or validated using the methods disclosed herein may be used for genome-based diagnostic and selection techniques; for tracing progeny of an organism; to determine hybridity of an organism; to identify variation of linked phenotypic traits, mRNA expression traits, or both phenotypic and mRNA expression traits; as genetic markers for constructing genetic linkage maps; to identify individual progeny from a cross wherein the progeny have a desired genetic contribution from a parental donor, recipient parent, or both parental donor and recipient parent; to isolate genomic DNA sequence surrounding a gene-coding or non-coding DNA sequence, for example, but not limited to a promoter or a regulatory sequence; in marker-assisted selection, map-based cloning, hybrid certification, fingerprinting, genotyping and allele specific marker; for transgenic plant development; and, as a marker in an organism of interest.

The primary motivation for developing molecular marker technologies from the point of view of plant breeders has been the possibility to increase breeding efficiency through marker assisted breeding. After positive markers have been identified through the statistical models described above, the corresponding genetic marker alleles can be used to identify plants that contain the desired genotype at multiple loci and would be expected to transfer the desired genotype along with the desired phenotype to its progeny. A molecular marker allele that demonstrates linkage disequilibrium with a desired phenotypic trait (e.g., a quantitative trait locus, or QTL) provides a useful tool for the selection of a desired trait in a plant population (i.e., marker assisted breeding).

A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus. Thus, a "marker allele," alternatively an "allele of a marker locus" is one of a plurality of polymorphic nucleotide sequences found at a marker locus in a population that is polymorphic for the marker locus. In some aspects, the present invention provides methods for identifying or validating marker loci correlating with a phenotypic trait of interest. Each of the identified markers is expected to be in close physical and genetic proximity (resulting in physical and/or genetic linkage) to a genetic element, e.g., a QTL, that contributes to the trait of interest.

In various embodiments of the present invention, the markers that are identified using the methods disclosed herein are used to select plants and enrich the plant population for individuals that have desired traits. The plant breeder can advantageously use molecular markers to identify desired individuals by identifying marker alleles that show a statistically significant probability of co-segregation with a desired phenotype. By identifying and selecting a marker allele (or desired alleles from multiple markers) that is optimized for the desired phenotype, the plant breeder is able to rapidly select a desired phenotype by selecting for the proper molecular marker allele.

The presence and/or absence of a particular genetic marker allele in the genome of a plant exhibiting a preferred phenotypic trait is determined by any method listed above, e.g., RFLP, AFLP, SSR, amplification of variable sequences, and ASH. If the nucleic acids from the plant hybridizes to a probe specific for a desired genetic marker, the plant can be selfed to create a true breeding line with the same genome or it can be introgressed into one or more lines of interest. The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

The marker loci identified or validated using the methods of the present invention can also be used to create a dense genetic map of molecular markers. A "genetic map" is a description of genetic linkage relationships among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. In contrast, a physical map of the genome refers to absolute distances (for example, measured in base pairs or isolated and overlapping contiguous genetic fragments, e.g., contigs). A physical map of the genome does not take into account the genetic behavior (e.g., recombination frequencies) between different points on the physical map.

In certain applications it is advantageous to make or clone large nucleic acids to identify nucleic acids more distantly linked to a given marker, or isolate nucleic acids linked to or responsible for QTLs as identified herein. It will be appreciated that a nucleic acid genetically linked to a polymorphic nucleotide sequence optionally resides up to about 50 centimorgans from the polymorphic nucleic acid, although the precise distance will vary depending on the cross-over frequency of the particular chromosomal region. Typical distances from a polymorphic nucleotide are in the range of 1-50 centimorgans, for example, often less than 1 centimorgan, less than about 1-5 centimorgans, about 1-5, 1, 5, 10, 15, 20, 25, 30, 35, 40, 45 or 50 centimorgans, etc.

Many methods of making large recombinant RNA and DNA nucleic acids, including recombinant plasmids, recombinant lambda phage, cosmids, yeast artificial chromosomes (YACs), PI artificial chromosomes, Bacterial Artificial Chromosomes (BACs), and the like are known. A general introduction to YACs, BACs, PACs and MACs as artificial chromosomes is described in Monaco & Larin, Trends Biotechnol. 12:280-286 (1994). Examples of appropriate cloning techniques for making large nucleic acids, and instructions sufficient to direct persons of skill through many cloning exercises are also found in Berger, Sambrook, and Ausubel, all supra.

In addition, any of the cloning or amplification strategies described herein are useful for creating contigs of overlapping clones, thereby providing overlapping nucleic acids which show the physical relationship at the molecular level for genetically linked nucleic acids. A common example of this strategy is found in whole organism sequencing projects, in which overlapping clones are sequenced to provide the entire sequence of a chromosome. In this procedure, a library of the organism's cDNA or genomic DNA is made according to standard procedures described, e.g., in the references above. Individual clones are isolated and sequenced, and overlapping sequence information is ordered to provide the sequence of the organism.

Once one or more QTLs have been identified that are significantly associated with the expression of the gene of interest, then each of these loci and linked markers may also be further characterized to determine the gene or genes involved with the expression of the gene of interest, for example, using map-based cloning methods as would be known to one of skill in the art. For example one or more known regulatory genes can be mapped to determine if the genetic location of these genes coincide with the QTLs controlling mRNA expression of the gene of interest. Confirmation that such a coinciding regulatory gene is effecting the expression of one or more genes of interest can be obtained using standard techniques in the art, for example, but not limited to, genetic transformation, gene complementation or gene knock-out techniques, or overexpression. The genetic linkage map can also be used to isolate the regulatory gene, including any novel regulatory genes, via map-based cloning approaches that are known within the art whereby the markers positioned at the QTL are used to walk to the gene of interest using contigs of large insert genomic clones. Positional cloning is one such a method that may be used to isolate one or more regulatory genes as described in Martin et al. (Martin et al., 1993, Science 262: 1432-1436; which is incorporated herein by reference).

"Positional gene cloning" uses the proximity of a genetic marker to physically define a cloned chromosomal fragment that is linked to a QTL identified using the statistical methods herein. Clones of linked nucleic acids have a variety of uses, including as genetic markers for identification of linked QTLs in subsequent marker assisted breeding protocols, and to improve desired properties in recombinant plants where expression of the cloned sequences in a transgenic plant affects an identified trait. Common linked sequences which are desirably cloned include open reading frames, e.g., encoding nucleic acids or proteins which provide a molecular basis for an observed QTL. If markers are proximal to the open reading frame, they may hybridize to a given DNA clone, thereby identifying a clone on which the open reading frame is located. If flanking markers are more distant, a fragment containing the open reading frame may be identified by constructing a contig of overlapping clones. However, other suitable methods may also be used as recognized by one of skill in the art. Again, confirmation that such a coinciding regulatory gene is effecting the expression of one or more genes of interest can be obtained via genetic transformation and complementation or via knock-out techniques described below.

Upon identification of one or more genes responsible for or contributing to a trait of interest, transgenic plants can be generated to achieve the desired trait. Plants exhibiting the trait of interest can be incorporated into plant lines through breeding or through common genetic engineering technologies. Breeding approaches and techniques are known in the art. See, for example, Welsh J. R., Fundamentals of Plant Genetics and Breeding, John Wiley & Sons, NY (1981); Crop Breeding, Wood D. R. (Ed.) American Society of Agronomy Madison, Wis. (1983); Mayo O., The Theory of Plant Breeding, Second Edition, Clarendon Press, Oxford (1987); Singh, D. P., Breeding for Resistance to Diseases and Insect Pests, Springer-Verlag, NY (1986); and Wricke and Weber, Quantitative Genetics and Selection Plant Breeding, Walter de Gruyter and Co., Berlin (1986). The relevant techniques include but are not limited to hybridization, inbreeding, backcross breeding, multi-line breeding, dihaploid inbreeding, variety blend, interspecific hybridization, aneuploid techniques, etc.

In some embodiments, it may be necessary to genetically modify plants to obtain a trait of interest using routine methods of plant engineering. In this example, one or more nucleic acid sequences associated with the trait of interest can be introduced into the plant. The plants can be homozygous or heterozygous for the nucleic acid sequence(s). Expression of this sequence (either transcription and/or translation) results in a plant exhibiting the trait of interest. Methods for plant transformation are well known in the art.

The following examples are offered by way of illustration and not by way of limitation.

EXPERIMENTAL EXAMPLES

Example 1

QTL Detection in a Nested Population

NAM is performed using SMR and MMR in combination with the permutation method described below to determine the LOD threshold for NAM.

Single Marker Regression (SMR):

The linear model to describe the relationship between trait values and marker genotypes is:

$$y_{ij} = \mu + x_{ij}a + g_i u_i + e_{ij} \quad \text{(model 1)}$$

where $y_{ij}$ is the phenotypic value of the individual j in the subpopulation i; $\mu$ is the overall mean; a is the additive effect of QTL; $g_i$ is the indicator variable of the subpopulation i; $u_i$ is the effect of the subpopulation i; $e_{ij}$ is the residual error; and, wherein $x_{ij}$ is defined as 1 if the individual j carries the allele from the common parent and −1 if the individual j carries the allele from the other parent.

The definition is based on the fact of there are only two distinct alleles for each marker. To exploit the simplicity of regression, the genetic background effect $u_i$ is assumed to be a fixed effect. Its inclusion into the model is to account for the influence from population stratification, and therefore reduce the residual variance.

The hypotheses to test QTL effect can be formulated as $H_0$: a=0 and $H_1$: $a_1 \neq 0$. The parameters under $H_0$ or $H_1$ are estimated by the least squares method based on the regression model depending on whether or not QTL effect is included in the SMR model. LR=−2($l_{reduced} - l_{full}$), where $l_{reduced}$ is the log likelihood of the reduced model, corresponding to $H_0$, and $l_{full}$ is that of the full model, corresponding to $H_1$ (Lander and Botstein 1989). Both are calculated from SMR model and a LOD score is calculated as LR/(2 ln 10). Note that the following MMR method uses the same hypothesis test and the method to calculate LOD.

This SMR method differs from the original marker-based regression method for NAM (Yu et al (2006) *Nature Genetics* 38(2):203-208) in the use of polymorphic markers. From NAM marker data, some markers show polymorphism in some subpopulations, but not in others. In this case, the inclusion of non informative markers may lead to segregation distortion of marker genotypes at that locus, and the distortion could cause the reduction of QTL mapping efficiency, power and precision. To avoid the problem, a marker-filtered procedure is incorporated into the SMR model to reduce the potential risk due to marker distortion. According to the present invention, only the phenotypic and genotypic data from those subpopulations with segregated genotypes of a marker are included in each analysis. Thus, in various embodiments of the invention, the subpopulations with non informative genotypes are excluded prior to SMR analysis. The procedure enables SMR to identify those alleles with very low frequency (less than 5%) in NAM.

Multiple Marker Regression (MMR):

To account for the influences from other QTLs, a MMR method was developed by using cofactor markers to absorb the effect of other QTLs. The linear model for MMR is $$y_{ij} = \mu + x_{ij}a + \Sigma(k=1,m)c_{ijk}b_k + g_i u_i + e_{ij} \quad \text{(model 2)}$$

wherein $y_{ij}$ is the phenotypic value of the individual j in the subpopulation i; wherein $\mu$ is the overall mean; wherein $x_{ij}$ is the genotype of QTL; wherein a is the additive effect of QTL; wherein $c_{ijk}$ is the cofactor marker k for the individual j in the subpopulation i; wherein $b_k$ is the effect of the cofactor marker k; wherein $g_i$ is the indicator variable of the subpopulation i; wherein $u_i$ is the effect of the subpopulation i; and, wherein $e_{ij}$ is the residual error.

Another aspect of the invention is the use of stepwise regression to select cofactor markers based on the significance level 0.01. The linear model used to choose cofactors is $$y_{ij} = \mu + c_{ijk}b_k + g_i u_i + e_{ij} \quad \text{(model 3)}$$

wherein $y_{ij}$ is the phenotypic value of the individual j in the subpopulation i; wherein $\mu$ is the overall mean; wherein $c_{ijk}$ is the cofactor marker k for the individual j in the subpopulation i; wherein $b_k$ is the effect of the cofactor marker k; wherein $g_i$ is the indicator variable of the subpopulation i; wherein $u_i$ is the effect of the subpopulation i; and, wherein $e_{ij}$ is the residual error. This stepwise regression model is different from the one used for conventional composite interval mapping (Zeng 1993, 1994) and the one originally used for NAM (Yu et al 2008). One aspect of the present invention performs stepwise regression for a NAM population with the inclusion of genetic backgrounds from different subpopulation into the model 3. This method selects those QTLs which have stable effects across multiple subpopulations. Stable effects refer to effects that are observed across multiple populations. The present invention also effectively reduces the number of cofactors included in the model, avoiding the problem of over saturation.

With cofactor markers, it is possible to obtain much clearer LOD profile from MMR than SMR. The use of cofactor markers is to reduce the residual error, and therefore increase the significance of QTL hypothesis test. MMR shows the ability to separate closely linked QTL analysis and to locate a QTL within a narrow genomic region.

However, MMR has difficulty in using a marker-filter procedure. This problem is caused by the singularity of design matrix used for the regression model. Thus, instead of filtering non informative marker, the present invention uses all genotypic data from all the subpopulations for data analysis. Based on this, the SMR and MMR will provide similar results for those markers with no distorted segregation, while they may show different results for the markers with skewed genotypic segregation. Thus, the invention is designed to perform both SMR and MMR as a complement combination for the NAM dataset.

Permutation Tests for NAM:

The original multiple regression method for NAM (Yu et al 2008) used a very low significance level $10^{-7}$ as a threshold for QTL detection. This method is not appropriate for determining LOD threshold at a given significance level, especially based on a dense linkage map. To solve this problem, the present invention uses a novel method of permutation tests to determine the empirical LOD threshold at the given significance level 0.05 and 0.01. The method reshuffles the phenotypic values within each subpopulation without destroying the structure of subpopulations and the correlation between different traits of interest. 1000 permutations are recommended to use for SMR and MMR. Out of these permutations, the LOD threshold at 0.05 and 0.01 levels are determined. Notice that 0.01 threshold may not be stable due to limited number of permutation tests (10000 permutations recommended).

Example 2

Method of Selection of Candidate Leads for Further Validation After Genome Wide Association Mapping With the advent of 'omics, identifying key candidates among the thousands of genes in a genome that play a role in a phenotype or a complex biological process has paradoxically become one of the main hurdles. Indeed, contrary to some early concerns that a lack of sufficient global data would still be a limiting factor, it is precisely the opposite, a bounty of information that now poses a challenge to scientists. This has translated into a need for sophisticated tools to mine, integrate and prioritize massive amounts of information. The present invention will help prioritize the candidate leads identified by Genome wide association mapping (using, for example, sequences from Solexa technology) for further validation and implementation in marker assisted breeding.

The nested association mapping population developed by the Maize Functional diversity group (Yu et al. Genetics 2008, 178: 539-551) is used for QTL mapping traits of interest. Since the linkage map has a resolution of ~1 cM (i.e. a marker density of 1 cM) the QTLs identified in this population should be very precise. The QTL mapping is done using the shared allele information of the parents that were used to develop the population. The sequences that are used for genome wide association mapping are positioned on the maize physical map. The markers on the NAM linkage map are also positioned on the maize physical map.

The QTLs identified in the NAM population are aligned on the physical map whenever the Solexa sequences and the QTLs from the NAM population overlap with each other. Those sequences from the Solexa sequencing are prioritized for further validation than the sequences that do not overlap with the QTLs identified in the NAM population. See FIG. 4.

Example 3

QTL Detection using NAM SMR and MMR

Experimental Design and Preparation of Phenotypic and Genotypic Data

The NAM RIL lines were planted across five locations within two years. The traits of interest, mainly including starch and protein in corn ethanol project, were evaluated across the locations and years. The phenotypic data from each location is unbalanced. The unbalanced data structure indicates that it is necessary to obtain the corresponding genotypic data for those lines. To do so, the genotype data was downloaded for all the markers (panzea.org/lit/data) and the genotypic information was extracted for the NAM lines evaluated. Also, to perform SMR and MMR, a consensus linkage map was found from the same website and downloaded for the further use.

Methods for Data Analysis

NAM SMR and MMR were used to detect the QTL responsible for starch and protein in corn. The details of these methods are described in Example 1. Both SMR and MMR are used for QTL mapping. SMR has an advantage to decrease the influences of marker segregation distortion, while MMR can localize a QTL within a narrow region on the chromosome. The combination of SMR and MMR maximizes the ability of QTL detection, while minimizing the risk of missing any QTL with minor effects.

Permutation methods have been developed for SMR and MMR so that the empirical LOD thresholds for the two methods can be determined at the given significance level 0.05. In this analysis, 1000 permutations were used to perform permutation tests for either one.

Results of QTL Mapping

Eleven QTL were found for corn starch trait and ten QTL for protein. Among these QTL, six QTL for starch were identified consistently across all the locations and five for protein. Also, 6 QTLs were found to control both starch and protein, indicating the potential pleiotropic effects for both traits. These six QTLs were found to have large effects on the individual traits. Identification of these pleiotropic QTL likely explains the strong phenotypic correlation between starch and protein in corn.

Conclusion

As expected, SMR and MMR identified the main and pleiotropic QTL for starch and protein based on NAM experimental design. Both methods are proven to be a powerful tool for QTL detection in NAM. The permutation methods for either method provided LOD thresholds for QTL detection.

Example 4

An Example of Genome-Wide Association Analysis in Combination with Linkage Mapping with Nested Association Mapping Populations for Prioritizing the Candidate Gene Leads for Biological Validation/Implementation Introduction Genome-wide association analysis (GWA) is a powerful tool for identifying common genetic variants in a population that affect traits of interest, offering high mapping resolution up to a single nucleotide change. Association study takes advantage of recombination events on the genome accumulated over many generations, which have segmented the genome into pieces of linkage disequilibrium (LD) blocks in the population. Markers on each of the LD blocks usually exhibit significant associations with functional changes in genes on the same blocks, and thus can be taken as proxies of the relevant functional changes in plant breeding, or as a basis for further pinpointing of the responsible genes.

The goal of GWA is to detect markers that are physically closely linked to the relevant functional changes. However it is common to detect associations of markers that are unlinked or distantly linked to the changes, which are usually considered as false positives. While many other population genetics factors (such as migration, mutation, genetic drift, non-random matting) might also contribute to false positive rate, population stratification or population structure has been identified as one of the major concerns that could cause a large number of false positives in GWA. Population structure exists when allele frequencies are systematically different among subpopulations in a population, which may be caused by migration and non-random mating, etc.

An Example for GWA

Samples and Data

1) Inbred panel for GWA: A maize inbred panel was assembled to include 600 inbred lines selected to maximize genetic diversity from a platform of about 3000 maize inbred lines. 450 of the lines in the panel are known to be derived from 3 subpopulations, namely non-stiff stalk (NSS), stiff stalk (SS), and tropical-subtropical (TS) subgroups; the remaining 150 lines have no available subgroup identity for various reasons in practice.

2) Genotypic data on 500,000 SNPs: Solexa sequencing technique was employed to screen the whole-genome cDNA libraries from 600 diverse inbred lines in the inbred panel for genome-wide SNPs, which identified about 500,000 high-quality SNPs.

3) Phenotypic data on 3 ethanol-related traits: The percentage contents of starch, oil, and protein in maize kernels, the 3 main ethanol related traits, were assessed with the Near Infrared Spectroscope (NIR) machine for each of the 600 inbreds in the inbred panel grown in 2 locations.

Data Preprocessing

Figure 5:
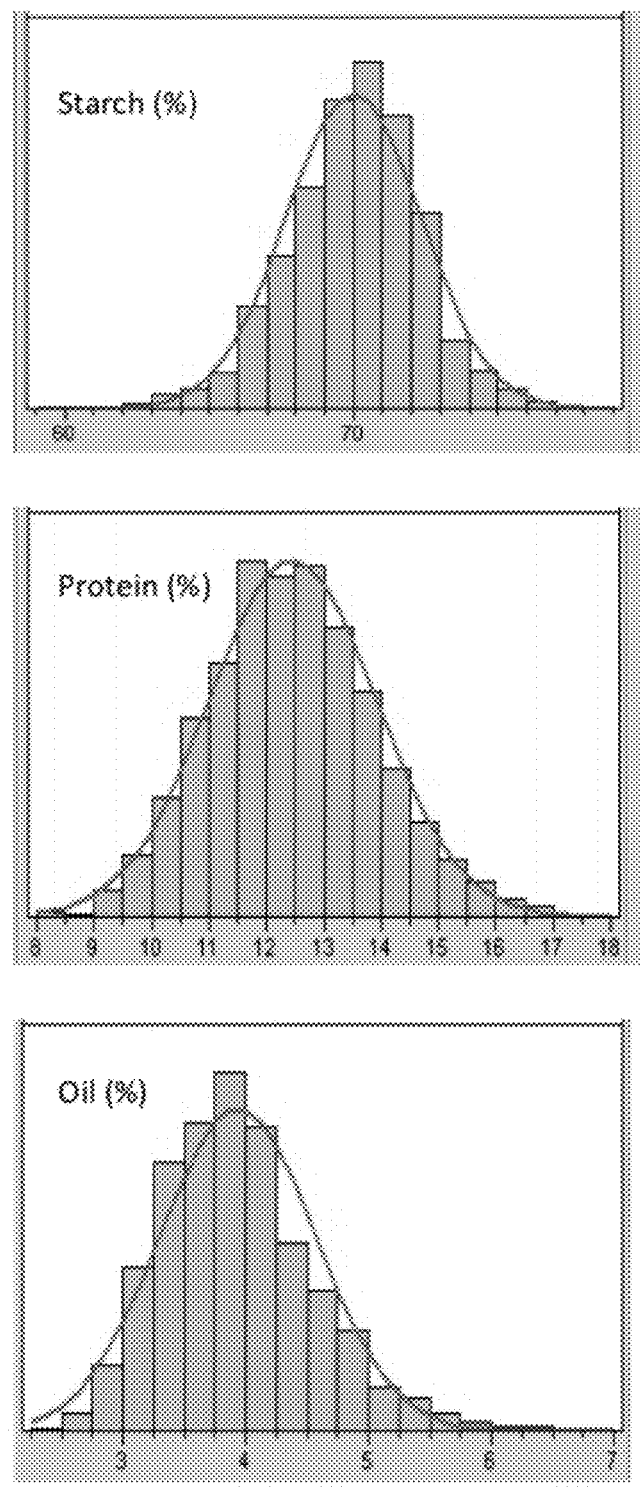
FIG. 5 shows histograms for 3 ethanol-related traits for 600 inbred lines in the inbred panel. The phenotypic data fitted well to normal distributions.

Phenotypic data was assessed to remove phenotyping suspicious data points empirically and statistically, such as outliers. Statistical distribution of the phenotypic data was also evaluated to determine if data transformation or permutations was needed for claiming significant marker-trait associations. As shown in the histogram for the trait (FIG. 5), these 3 traits are approximately normally distributed, which suggests that p values estimated from the association tests that rely on normal assumption will be basically valid.

Genotypic data were evaluated to identify obvious errors, e.g. more than 2 alleles for a SNP marker, and uninformative SNPs (monomorphic or those with a minor allele frequency<0.05). Among the 500,000 SNPs, 1200 SNPs were uninformative and excluded from the data. Hardy-Weinberg equilibrium could not be tested for an inbred population because there is inherent deficiency of heterozygotes in the population.

Phenotypic Data Adjustment for Individual Inbred Lines

A mixed-linear model approach was used to obtain the total genetic value for each inbred line in the sample with control of effects from locations and randomized blocks. In this model, the total genetic effect for each inbred line is taken as random because the inbred lines used in the panel are considered as a random sample from the whole germplasm; the randomized blocks are also considered as random; the locations are taken as fixed effects, which are the target locations for any future hybrids to be grown. The statistical model for the analysis can be written as $$Y_{hijk}=\mu+G_h+L_i+B_{j(i)}+e_{hijk}$$

where $\mu$ is the general mean; $G_h$ is the total random genetic effect for the h-th inbred; $L_i$ is the fixed effect for location i; $B_{j(i)}$ is the random block effect for block j in location i; $e_{hijk}$ is the random residual, assumed to be normally distributed. This model is fitted in statistical package R with the lme4 library (www.r-project.org).

The best linear unbiased predicted (BLUP) values for $G_h$ are obtained and used as the phenotypic data in the mixed-linear-model association approach as implemented in software TASSEL.

Estimation of Population Structure

Inclusion of population structure in statistical models can effectively reduce false positives in association analysis. TASSEL incorporates population structure as a model factor in the mixed linear model to achieve this goal.

As mentioned previously, there are 3 known subpopulations (SS, NSS, and TS) in the inbred panel, but 25% of the inbreds have no subpopulation identity. One way around this is to estimate the population structure for the inbred panel with the SNP data for the inbreds. A random set of 2000 SNPs were selected from all the informative SNPs, and used for the estimation of population structure.

As described in U.S. patent application Ser. No. 12/328,689, filed Dec. 4, 2008, principle component analysis (PCa-lif.) offers similar accuracy in population structure estimation to the Bayesian approach in STRUCTURE. PCA was conducted with all the SNP data, and obtained the top 50 principal components (PC) and their eigenvectors were obtained. Trait-specific contributing principal components out of the 50 PCs were selected with stepwise regression analysis, which has been shown to provide a better control of population structure effects than simply using a few top PCs in the association mixed model.

Estimation of Kinship Coefficients

Kinship coefficient is a measure of relatedness between two individuals. It represents the probability that two genes, sampled at random from each individual are identical by descent. There are a number of methods for estimating kinship coefficients with marker data, each having advantages and disadvantages. The proportion of shared alleles across all SNP loci was chosen as the measure of kinship coefficient between a pair of inbred lines, which is essentially the probability of two random genes identical by state. Such kinship coefficients were calculated for all possible pairs of lines.

Association Analysis with a Mixed Model Approach

Mixed linear models have been applied to association mapping in plants (Yu et al. 2006, Nature Genetics), which has been shown superior in controlling population structure. This approach was implemented in ASReml (Gilmour et al. (1995) *Biometrics* 51:1440-1450), a commercial software package for executing general mixed models, through a comprehensive Perl script that provides full automation of data analysis for multiple traits. Compared with TASSEL, the software implementing the mixed model approach by Yu et el. (2006, Nature Genetics, Vol 38: 203-208), ASReml is much faster and the Perl script minimizes the user attention.

The mixed linear model implemented in ASReml is the same as in TASSEL, which can be written in matrix form as $$y=X\beta+S\alpha+Qv+Zu+e \quad \text{var}(y)=ZKZ'\sigma^2_v+R\sigma^2_e$$

where y is the vector for phenotypic values of all unique inbred lines; $\beta$ is the vector for all fixed experimental effects, $\alpha$ is the vector for the genetic effects of the putative QTL at the test position; v is the vector for subpopulation effects; u is the vector for polygenic effects of individual inbreds; e is the random residual vector. X, S, Q, and Z are known incidence matrices.

In this analysis, the adjusted phenotypic data (total genetic effects) were used as y, the 10 PCA eigenvectors were used as Q matrix; X matrix is essentially a vector of is for the general mean; S is the genotype matrix under additive genetic model for each SNP under test; Z is the incidence matrix for the set of unique inbred lines.

Association Results

A p value was calculated for testing the significance of each informative SNP in the association analysis, along with the phenotypic contribution R square and a few other statistics. Both false discovery rate (FDR) and Bonferroni correction were used to control false positives inflated with multiple tests. The nominal p value at the significance level (alpha) with Bonferroni correction was calculated as alpha/number of tests (SNPs); the FDR threshold was derived from the estimated p value distribution. The average between the two thresholds at the same significance level (alpha) was used.

Alpha=0.05 was chosen as the significance level for all of the tests. This resulted in 102 SNPs significantly associated with starch content, 134 SNPs associated with protein, and 97 SNPs associated with oil. These SNPs were found to be from 30, 35, and 23 linkage disequilibrium blocks on the genome, respectively, for starch, protein, and oil.

Overlay of GWA Associations with Linkage Mapping Results from NAM

Statistically significant associations may not always indicate true biological associations, possibly due to sampling errors. Therefore, evidence from independent sources may be helpful for validating the detected associations.

Nested association mapping (NAM) populations in maize, as a new type of mapping population, were made available publicly (Yu et al. 2008, Genetics, and Vol. 178: 539 55 1). The advantage of this type of population is that it offers promise of higher statistical power and mapping resolution than linkage mapping, but less false positives than association mapping with samples from a general population. Linkage mapping study for starch with the NAM populations has been done previously (Example 3 mentioned above), from which 11 QTL regions were identified for starch, 10 for protein, and 8 for oil.

Figure 4:
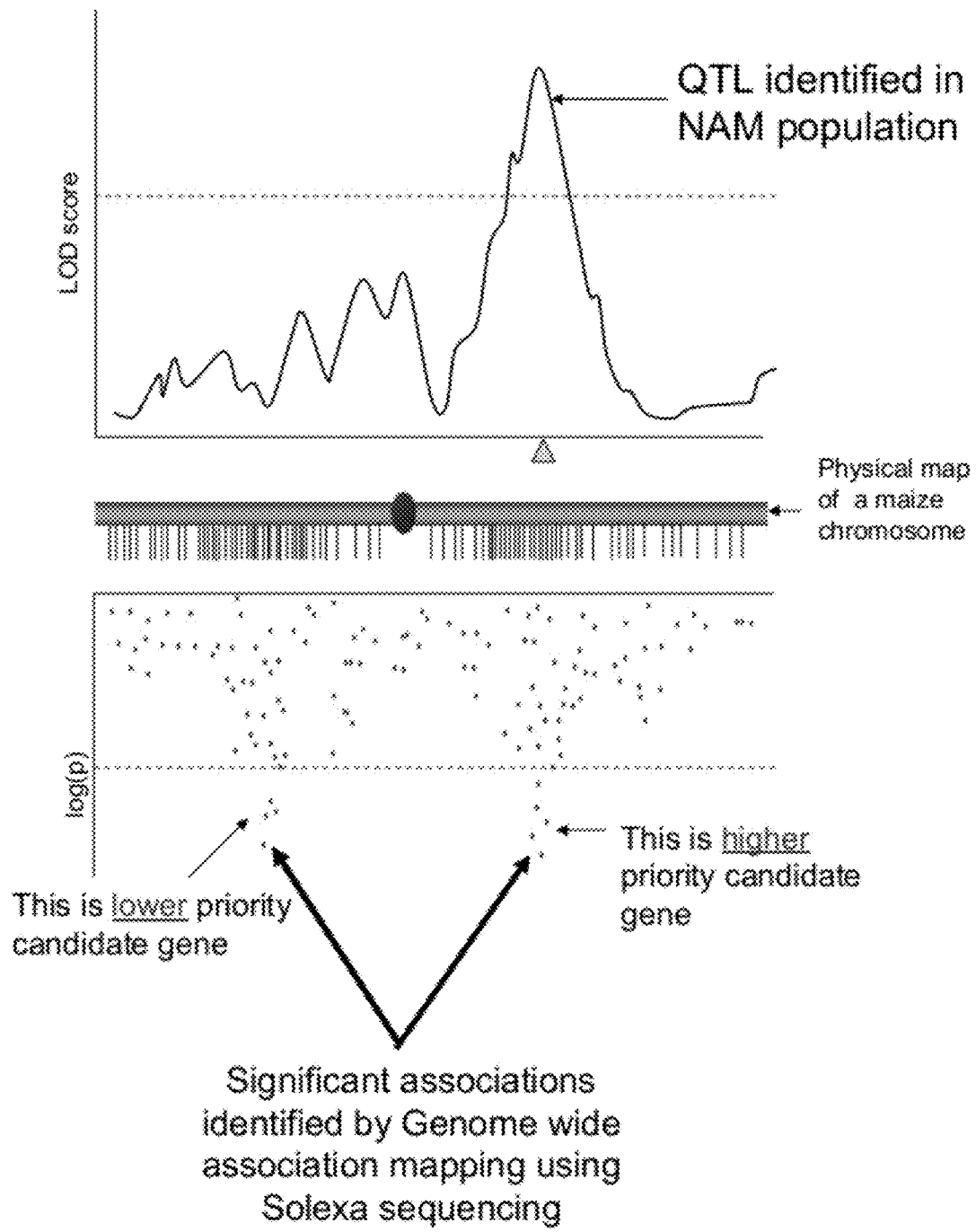
FIG. 4 is an exemplary schematic representation of selection and prioritization based on overlapping markers identified using NAM (top panel) and GWA (bottom panel).

The method to overlay the associated SNPs from GWA to the detected QTL regions from NAM linkage analysis was to put the associated SNPs and the markers in the QTL regions on the same physical map and a consensus genetic map (see FIG. 4). Table 1 indicates that 55% of all the associated SNPs were contained in 8 QTL regions for starch; 31.1% of associated SNPs contained in 6 QTL for protein, 27.8 of all the associated SNPs contained in 3 QTLs.

TABLE 1

Summary of overlapping QTL and associated SNPs

| Trait | All NAM QTLs | All GWA associated SNPs | Overlapping QTL | Overlapping SNPs | Overlapping SNP % |
|---|---|---|---|---|---|
| Starch (%) | 11 | 102 | 8 | 41 | 40.2 |
| Protein (%) | 10 | 134 | 6 | 33 | 24.6 |
| Oil (%) | 8 | 97 | 3 | 27 | 27.8 |

The SNPs from the genes that are overlapping with the QTLs detected in the NAM population are given a higher priority and will be used for further biological validation. These SNPs are also used for downstream applications such as marker assisted breeding.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of identifying a genetic marker associated with a trait of interest in a nested population of non-human organisms comprising:
    a) providing a genotypic value for each of a plurality of genetic markers for each member of said nested population, wherein said population comprises members exhibiting said trait of interest;
    b) providing a phenotypic value for said trait of interest for each member of said population; and
    c) determining whether one or more of said genetic markers is associated with the trait of interest using a nested association model comprising a combination of a single marker regression (SMR) model and a multiple marker regression (MMR) model, wherein:
        i) noninformative genotypes are removed prior to using the SMR model to evaluate an association between a trait value and a marker genotype; and
        ii) stepwise regression is used to select cofactor markers for inclusion in the MMR model,
    wherein a genetic marker is considered to be associated with the trait of interest if either the SMR model or the MMR model detects an association and wherein step (c) is performed on a suitably programmed computer.

2. The method of claim 1, wherein said SMR model comprises:

$$y_{ij}=\mu+x_{ij}a+g_iu_i+e_{ij}$$

wherein $y_{ij}$ is the phenotypic value of the individual j in the subpopulation i;
wherein $\mu$ is the overall mean;
wherein a is the additive effect of QTL;
wherein $g_i$ is the indicator variable of the subpopulation i;
wherein $u_i$ is the effect of the subpopulation i;
wherein $e_{ij}$ is the residual error; and
wherein $x_{ij}$ is defined as 1 if the individual j carries the allele from a tester or an elite parent and −1 if the individual j carries the allele from an inbred parent or an exotic parent.

3. The method of claim 1, wherein said MMR model comprises:

$$y_{ij}=\mu+x_{ij}a+\Sigma(k=1,m)c_{ijk}b_k+g_iu_i+e_{ij}$$

wherein $y_{ij}$ is the phenotypic value of the individual j in the subpopulation i;
wherein $\mu$ is the overall mean;
wherein $x_{ij}$ is the genotype of the QTL;
wherein a is the additive effect of QTL;
wherein m is total number of cofactors;
wherein $c_{ijk}$ is the cofactor marker k for the individual j in the subpopulation i;
wherein $b_k$ is the effect of the cofactor marker k;
wherein $g_i$ is the indicator variable of the subpopulation i;
wherein $u_i$ is the effect of the subpopulation i; and,
wherein $e_{ij}$ is the residual error.

4. The method of claim 1, wherein the cofactor markers are selected based on defined significance level.

5. The method of claim 4, wherein said significance level is less than or equal to 0.1.

6. The method of claim 4, wherein cofactors are selected using a model comprising:

$$y_{ij}=\mu+c_{ijk}b_k+g_iu_i+e_{ij}$$

wherein $y_{ij}$ is the phenotypic value of the individual j in the subpopulation i;
wherein $\mu$ is the overall mean;
wherein $c_{ijk}$ is the cofactor marker k for the individual j in the subpopulation i;
wherein $b_k$ is the effect of the cofactor marker k;
wherein $g_i$ is the indicator variable of the subpopulation i;
wherein $u_i$ the effect of the subpopulation i; and,
wherein $e_{ij}$ is the residual error.

7. The method of claim 1, wherein said nested population is an inbred population resulting from a cross between a single common parent line and each of a plurality of founder lines.

8. The method of claim 7, wherein said population comprises a population resulting from one or more rounds of self-crossing of the progeny of the cross between said single common parent and each of said plurality of founder lines.

* * * * *

UNITED STATES PATENT AND TRADEMARK OFFICE
CERTIFICATE OF CORRECTION

PATENT NO. : 8,170,805 B2
APPLICATION NO. : 12/367045
DATED : May 1, 2012
INVENTOR(S) : Kishore et al.

It is certified that error appears in the above-identified patent and that said Letters Patent is hereby corrected as shown below:

Column 13, Line 48: begin a new paragraph at "Marker data at regular intervals"

Column 15, Line 31: correct "biosun01.biostatjh"
to read -- biosun01.biostat.jh --
Line 65: correct "in QIPDT 1," to read -- in QIPDT1, --

Column 18, Line 2: correct "mean; a is the additive"
to read -- mean; $a$ is the additive --

Column 19, Line 23: correct "QTL; a is the additive"
to read -- QTL; $a$ is the additive --

Column 20, Line 34: correct "a=0 and $H_1$: $a_1 \neq 0$."
to read -- $a=0$ and $H_1$: $a_1 \neq 0$. --
Line 52: correct "LR= $-2(l_{reduced}-l_{full})$ where $l_{reduced}$"
to read -- LR= $-2(\ell_{reduced} - \ell_{full})$ where $\ell_{reduced}$ --
Line 54: correct "and $1_{full}$ is" to read -- and $\ell_{full}$ is --

Column 27, Line 31: correct "mean; a is the additive"
to read -- mean; $a$ is the additive --
Line 44: correct "a=0 and $H_1$: $a_1=0$."
to read -- $a=0$ and $H_1$: $a_1=0$. --
Line 47: correct " LR= $-2(l_{reduced}-l_{full})$ where $l_{reduced}$ "
to read -- LR= $-2(\ell_{reduced} - \ell_{full})$ where $\ell_{reduced}$ --
Line 49: correct " $1_{full}$ is " to read -- $\ell_{full}$ is --

Signed and Sealed this
Eighteenth Day of September, 2012

David J. Kappos
*Director of the United States Patent and Trademark Office*

CERTIFICATE OF CORRECTION (continued)
U.S. Pat. No. 8,170,805 B2

Column 28, Line 13: correct "wherein a is the additive"
                to read -- wherein $a$ is the additive --

Column 32, Lines 4-5: correct "analysis (PCa-lif.) offers"
                to read -- analysis (PCA) offers --
      Line 50: correct "a vector of is for the general"
                to read -- a vector of 1s for the general --

Column 33, Line 11: correct "Vol. 178: 539-55 1)"
                to read -- Vol. 178: 539-551) --

Column 34, Claim 2, Line 19: correct "wherein a is the additive"
                      to read -- wherein $a$ is the additive --
      Claim 3, Line 34: correct "wherein a is the additive"
                      to read -- wherein $a$ is the additive --
      Claim 6, Line 56: correct "wherein $u_i$ the effect"
                      to read -- wherein $u_i$ is the effect --